United States Patent
Eliasen et al.

[11] Patent Number: 6,086,555
[45] Date of Patent: Jul. 11, 2000

[54] DUAL RESERVOIR VASCULAR ACCESS PORT WITH TWO-PIECE HOUSING AND COMPOUND SEPTUM

[75] Inventors: Kenneth A. Eliasen, West Jordan; Kelly B. Powers, North Salt Lake; Ronald O. Campbell, Farmington; Guy T. Rome, West Valley City, all of Utah; Kelly J. Christian, Pocatello, Id.

[73] Assignee: C. R. Bard, Inc., Murray Hill, N.J.

[21] Appl. No.: 09/025,695

[22] Filed: Feb. 18, 1998

Related U.S. Application Data

[63] Continuation-in-part of application No. 08/784,580, Jan. 17, 1997, Pat. No. 5,833,654.

[51] Int. Cl.[7] .................................................. A61M 5/00
[52] U.S. Cl. ............................................. 604/93; 604/175
[58] Field of Search ............................ 604/93, 175, 174, 604/116, 500, 513, 523

[56] References Cited

U.S. PATENT DOCUMENTS

| | | | |
|---|---|---|---|
| 4,692,146 | 9/1987 | Hilger | 604/93 |
| 4,695,273 | 9/1987 | Brown | 604/173 |
| 4,710,174 | 12/1987 | Moden et al. | 604/175 |
| 4,767,410 | 8/1988 | Moden et al. | 604/175 |
| 4,772,270 | 9/1988 | Wiita et al. | 604/175 |
| 4,772,276 | 9/1988 | Wiita et al. | 604/283 |
| 4,778,452 | 10/1988 | Moden et al. | 604/93 |
| 4,892,518 | 1/1990 | Cupp et al. | 604/93 |
| 4,900,312 | 2/1990 | Nadeau | 604/246 |
| 4,915,690 | 4/1990 | Cone et al. | 604/93 |
| 5,084,015 | 1/1992 | Moriuchi | 604/96 |
| 5,090,954 | 2/1992 | Geary | 604/29 |
| 5,108,377 | 4/1992 | Cone et al. | 604/93 |
| 5,167,638 | 12/1992 | Felix et al. | 604/175 |
| 5,213,574 | 5/1993 | Tucker | 604/93 |
| 5,306,255 | 4/1994 | Haindl | 604/175 |
| 5,360,407 | 11/1994 | Leonard | 604/175 |
| 5,387,192 | 2/1995 | Glantz et al. | 604/93 |
| 5,395,324 | 3/1995 | Hinrichs et al. | 604/86 |
| 5,399,168 | 3/1995 | Wadsworth, Jr. et al. | 604/175 |
| 5,421,814 | 6/1995 | Geary | 604/4 |
| 5,558,641 | 9/1996 | Glantz et al. | 604/93 |
| 5,562,617 | 10/1996 | Finch, Jr. et al. | 604/93 |
| 5,562,618 | 10/1996 | Cai et al. | 604/93 |
| 5,613,945 | 3/1997 | Cai et al. | 604/93 |
| 5,632,729 | 5/1997 | Cai et al. | 604/93 |
| 5,647,855 | 7/1997 | Trooskin | 604/175 |
| 5,688,237 | 11/1997 | Rozga et al. | 604/53 |
| 5,704,915 | 1/1998 | Melsky et al. | 604/175 |
| 5,792,104 | 8/1998 | Speckman et al. | 604/93 |
| 5,833,654 | 11/1998 | Powers et al. | 604/93 |

FOREIGN PATENT DOCUMENTS

WO 98/31417  7/1998  WIPO .......................... A61M 39/00

*Primary Examiner*—John D. Yasko
*Attorney, Agent, or Firm*—Trask, Britt & Rossa

[57] ABSTRACT

A vascular access port enclosing a pair of distinct fluid reservoirs includes a two-piece housing that captures an integrally-formed compound septum to seal both of the fluid reservoirs for selective access with a hypodermic needle. The housing includes a base that defines the fluid reservoirs and a cap in which the base is received with the compound septum therebetween. The compound septum includes two distinct target domes that are exposed to the exterior of the housing through respective access apertures in the cap, when the compound septum is captured in the housing. A planar septum web interconnects and encircles the target domes. The side of the septum web opposite from the target domes is formed into a recessed isolation groove that traverses the septum web between the target domes. Sealing ridges depend from this side of the septum web on either side of the isolation groove. The outlet stem of the access port is integrally formed with the base of the housing. In the base an open-topped fluid channel communicates from each fluid reservoir to a corresponding enclosed fluid passageway in the outlet stem. The open top of each fluid channel is closed by a portion of the compound septum captured in the housing.

51 Claims, 22 Drawing Sheets

DUAL RESERVOIR VASCULAR ACCESS PORT WITH TWO-PIECE HOUSING AND COMPOUND SEPTUM

RELATED APPLICATIONS

This application is a continuation-in-part application of U.S. patent application Ser. No. 08/784,580 that was filed on Jan. 17, 1997 now U.S. Pat. No. 5,833,654.

BACKGROUND

1. The Field of the Invention

The present invention relates to vascular access systems, and more specifically to implantable vascular access ports for use in such systems. The present invention pertains in particular to such vascular access ports as enclose distinct first and second fluid reservoirs and are, therefore, suited for interconnection with a dual lumen catheter when utilized in a vascular access system.

2. Background Art

Implantable vascular access systems are used extensively in the medical field to facilitate the performance of recurrent therapeutic tasks inside the body of a patient. Such a vascular access system generally includes a vascular access port that is attached to the proximal end of a vascular access catheter.

The use of a dual lumen vascular access catheter in such a system enhances the utility of the system by, for example, permitting the withdrawal of fluid through one lumen of the catheter, while affording the opportunity simultaneously to infuse fluid through the other lumen. Medications that react adversely with each other are frequently called for in a course of therapy. The use of a vascular access system having a dual lumen catheter is also particularly advantageous under such circumstances, as each of the incompatible medications can be isolated from the other by consistently using each in a different lumen in the dual lumen catheter of the system. Each medication can then be infused as required in the lumen identified thereto without any risk of adverse reaction with residue of the other medication that might have remained in the system from a previous infusion.

A vascular access port for use in a vascular access system employing a dual lumen catheter typically has a needle-impenetrable housing that encloses distinct first and second fluid reservoirs and defines for each such fluid reservoir a corresponding access aperture that communicates through the housing on the side thereof that is adjacent to the skin of the patient, when the access port has been implanted in the body of a patient. Each access aperture is sealed by a distinct needle-penetrable elastomeric septum.

Such a dual reservoir vascular access port also includes an outlet stem, which projects from the housing of the access port and encloses a longitudinally extending fluid flow passageway corresponding to and communicating with each of the fluid reservoirs in the housing. Using the outlet stem, the distal end of the dual lumen catheter can be mechanically coupled to the access port with each lumen of the catheter in a fluid-tight communication with an individual of the fluid reservoirs therein.

The entirety of the vascular access system, both the dual reservoir vascular access port and the dual lumen catheter attached thereto, is implanted in the body of the patient. The distal tip of the catheter is disposed at a predetermined location where therapeutic activity is to be effected. Once the vascular access system has been implanted, a non-coring hypodermic needle can be employed selectively and repeatedly to access each of the fluid reservoirs of the access port. To do so, the tip of the hypodermic needle is advanced through the skin of the patient at the implantation site for the access port and then used to penetrate a selected one of the septums of the access port itself The syringe associated with the hypodermic needle can infuse medication or other fluids into the body of the patient at the distal tip of the catheter of the system. Such materials are made to flow down the hypodermic needle from the syringe, through the fluid reservoir accessed by the tip of the hypodermic needle, out of the access port through the corresponding fluid flow passageway in the outlet stem, and along one of the lumens of the dual lumen catheter to the distal tip thereof Alternatively, the syringe is able to aspirate body fluids from the vicinity of the distal tip of the catheter. By withdrawing the syringe of the hypodermic needle, a negative pressure is created in the fluid reservoir that has been accessed. This causes bodily fluids in the vicinity of the distal tip of the catheter to be withdrawn along a lumen of the catheter of the system, into the access port through the outlet stem thereof, and by way of the fluid reservoir being accessed, up the hypodermic needle into the syringe.

Such a dual reservoir vascular access port is illustrated in full detail in U.S. Pat. No. 5,399,168. The dual reservoir vascular access port disclosed therein includes a three-piece needle-impenetrable housing comprising a base, a septum support, and a cap, all configured so as to be capable of being fixedly engaged with each other.

The base has a flat floor and walls normal and upstanding therefrom that define a first fluid reservoir and a second fluid reservoir distinct therefrom.

The septum support is planar and configured to mate with the ends of the walls of the base opposite from the floor of the base. The septum support has formed therethrough a first septum receiving aperture positioned above the first fluid cavity and a distinct second septum receiving aperture positioned above the second fluid cavity.

The cap is configured to receive the septum support and the base, thereby forming the exterior of the upper portion of the housing. The cap includes a top wall and a depending skirt that encloses the septum support and the walls of the base in the assembled condition of the housing. Formed through the top wall of the cap are distinct first and second septum access apertures that are located opposite, respectively, the first and the second septum receiving apertures in the septum support.

An outlet stem enclosing two longitudinally extending fluid flow passageways projects from the base of the housing and through the skirt of the cap. The fluid flow passageways in the outlet stem communicate through corresponding individual exit passageways with individual of the fluid reservoirs in the housing.

In assembling the dual reservoir vascular access port disclosed in U.S. Pat. No. 5,399,168, a pair of identical disc-shaped needle-penetrable elastomeric septums is captured between the septum support and the cap of the housing. Each septum seals a respective fluid reservoir by filling the septum access aperture and septum receiving aperture associated therewith. The dual reservoir vascular access port itself thus includes five (5) components: three (3) needle-impenetrable housing elements and two (2) needle-penetrable septums.

A known dual reservoir vascular access port that attempts to reduce the number of these components is shown in FIG. 1. There can be seen a dual reservoir vascular access port 10 for use in a vascular access system with a dual lumen catheter 12. The coupling of dual lumen catheter 12 to dual reservoir access port 10 is effected by a catheter connection system 14 that is seen in the disassembled state thereof in FIG. 2 to include an outlet stem 16 that is received in the lumens of catheter 12 and a locking sleeve 18 that is slid freely along the outer surface of catheter 12 toward access port 10 and onto the portion of catheter 12 in which outlet stem 16 has been received.

FIG. 2 also illustrates in exploded perspective view the components of access port 10 itself These include a cap 26, a base 20 that encloses a first fluid reservoir 22 and a second fluid reservoir 24, and distinct needle-penetrable elastomeric septums 28, 30 that are disc-shaped. Septums 28, 30 are supported directly on base 20 and retained there by cap 26, sealing access to fluid reservoirs 22, 24, respectively. Septums 28, 30 are exposed to the exterior of access port 10 through respective of septum access openings 32, 34, that are formed through a top wall 36 of cap 26. The tip of a non-coring hypodermic needle is, as a result, capable of accessing either of fluid reservoirs 22, 24 by piercing a corresponding one of septums 28, 30.

Taken alone FIG. 2 would tend to suggest that access port 10 is comprised of only four components: two (2) needle-impenetrable housing elements, and two (2) needle-penetrable septums. This economy in components is, however, actually achieved by constructing base 20 from two (2) separate elements made of dramatically different materials. While cap 26 and most of base 20 are made of injection moldable plastic, outlet stem 16 is fabricated necessarily using the complex machining required with a metallic material, such as titanium. The plastic portion of base 20 is injection molded about outlet stem 16 with outlet stem 16 projecting outwardly from base 20 between fluid reservoirs 22, 24.

The partial breakaway view presented in FIG. 3 depicts outlet stem 16 and the portion of base 20 immediately adjacent thereto. An embedded portion 38 of outlet stem 16 can there be seen to be secured within the material of base 20. This occurs during the injection molding of base 20. Embedded portion 38 of outlet stem 16 extends through the material of base 20 to comprise a portion of the interior sidewalls of each of fluid reservoirs 22, 24. The portion of outlet stem 16 external of base 20 includes a pair of outlet prongs 40, 42 separated by an elongated slot 44.

FIG. 4 reveals the internal structure of outlet stem 16. Fluid flow passageways 46, 48 are formed longitudinally within each of outlet prongs 40, 42, respectively. Fluid flow passageway 46 communicates with first fluid flow reservoir 22 through a rear channel 50 that is entirely formed within embedded portion 38 of outlet stem 16. Similarly, fluid flow passageway 48 communicates with second fluid reservoir 24 through a rear channel 52 that is also formed through embedded portion 38 of outlet stem 16.

Accordingly, access port 10 actually comprises five (5) components: two (2) needle-penetrable septums, two needle-impenetrable plastic housing components, and a metal outlet stem that is partially embedded in one of those housing components. Somewhat disadvantageously, the labor costs associated with the manufacture of a metal outlet stem, such as outlet stem 16, dwarf the labor costs associated with the plastic and needle-penetrable components of access port 10.

As a result, access port 10 is less economical than even the access port disclosed in U.S. Pat. No. 5,399,168 and mentioned previously.

SUMMARY OF THE INVENTION

It is, therefore, a general objective of the present invention to provide an improved dual reservoir vascular access port.

It is, however, also an object of the present invention to increase the public availability of dual reservoir vascular access ports, particularly by careful attention to maintaining the cost of such devices at a level that is accessible to the general public.

Therefore, a primary object of the present invention is to elevate the design sophistication associated with dual reservoir vascular access ports and correspondingly to refine the methods used to manufacture such devices.

In that regard, it is one object of the present invention to reduce the number of components required in the assembly of a dual reservoir vascular access port.

Relatedly, it is also an object of the present invention to temper the labor costs associated with the manufacture of dual reservoir vascular access ports.

Yet another object of the present invention is to provide a design for the housing of a dual reservoir vascular access port that is simple to construct and that benefits fully in manufacturing from the properties of the material of which that housing can be manufactured.

Another object of the present invention is to free the design of dual reservoir vascular access ports from reliance upon components that must be made of materials, such as titanium, that are relatively difficult and time consuming to shape at scales appropriate in such access ports.

An additional object of the present invention is to produce new configurations for the needle-penetrable material used to seal from the exterior of a dual lumen vascular access port the plurality of fluid reservoirs enclosed therein.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein a dual reservoir vascular access port is provided that includes a needle-impenetrable base, a needle-impenetrable cap configured to receive the base, and a needle-penetrable elastomeric compound septum. The base of the access port includes a footing, an encircling sidewall upstanding from the footing, and an interior wall also upstanding from the footing. The interior wall interconnects a pair of non-adjacent locations on the interior of the encircling sidewall. In this manner, a first fluid reservoir having a first inner floor and a second fluid reservoir having a second inner floor are defined inside of the encircling sidewall, but on opposite sides of the interior wall.

The cap of the access port includes a top wall and an encircling skirt that depends from the top wall. A first access aperture is formed through the top wall at a position that communicates with the first fluid reservoir, when the base is received in the cap. Correspondingly, a second access aperture is formed through the top wall at a position that communicates with the second fluid reservoir, when the base is received in the cap.

The compound septum of the access port includes a first target dome, a second target dome, and a septum web that is integrally formed with and interconnecting of the first target dome and the second target dome. When the base is received in the cap with the compound septum disposed therebetween, the first target dome is disposed in the first access aperture, and the second target dome is disposed in the second access aperture. The septum web is so configured as to effect the fluid isolation of the first fluid reservoir from the second fluid reservoir.

The side of the septum web opposite from the first target dome and the second target domes defines a lower surface of the septum web. Into that lower surface is recessed an isolation groove that traverses the septum web between the first target dome and the second target dome. Also, a first sealing ridge depends from the lower surface of the septum web, while a second sealing ridge depends from the lower surface on the side of the isolation groove opposite from the first sealing ridge.

An outlet stem integrally formed with the base of the access port projects from the exterior of the sidewall of the base. The outlet stem encloses a first fluid passageway and a second fluid passageway that extend longitudinally through the outlet stem in a side-by-side relationship. An open-topped first fluid channel communicates between the first fluid reservoir of the access port and the proximal end of the first fluid passageway of the outlet stem. Similarly, an open-topped second fluid channel communicates between the second fluid reservoir of the access port and the proximal end of the second fluid passageway of the outlet stem. When the base of the access port is received in the cap with the compound septum therebetween, a portion of the lower surface of the septum web of the compound septum closes the open top of the first fluid channel and the open top of the second fluid channel.

The benefits of such a relationship are also obtainable where a pair of distinct septums is utilized with a base of an access port as described above. Under such circumstances the advantage of utilizing a single, integrally formed needle-penetrable article to seal both of the distinct fluid reservoirs in a dual reservoir vascular access port is sacrificed. Nonetheless, if each of the distinct first and second septums includes a corresponding needle dome and an encircling septum web integrally formed therewith, then the lower surface of the septum web associated with the distinct first septum closes the open top of the first fluid channel, while the lower surface of the septum web associated with the distinct second septum closes the open top of the second fluid channel.

In a preferred embodiment, each of the first fluid channel and the second fluid channel is substantially linear, having parallel sides that are perpendicular to the floor of the respective fluid reservoir with which each fluid channel communicates. The longitudinal axis of the first fluid channel is disposed at an acute angle to the longitudinal axis of the respective fluid passageway in the outlet stem with which each fluid channel communicates.

In one aspect of the present invention, a compound septum for use in an implantable dual reservoir vascular access port comprises not only a first needle-penetrable target dome, a second needle-penetrable target dome, and an interconnecting septum web integrally formed therewith, but reservoir segregation means on the lower side of the septum web. The reservoir segregation means isolates the first fluid reservoir of the access port from the second fluid reservoir. By way of example and not limitation, structures capable of performing the function of the reservoir segregation means may include an isolation groove recessed into and traversing the lower side of the septum web. In addition thereto, a first sealing ridge depends from the lower side of the septum web between the isolation groove and the first target dome, while a second sealing ridge depends from the lower side of the septum web between the isolation groove and the second target dome.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention will be described and explained with additional specificity and detail through the use of the accompanying drawings in which.

DESCRIPTION OF THE PREFERRED EMBODIMENTS

Figure 1:
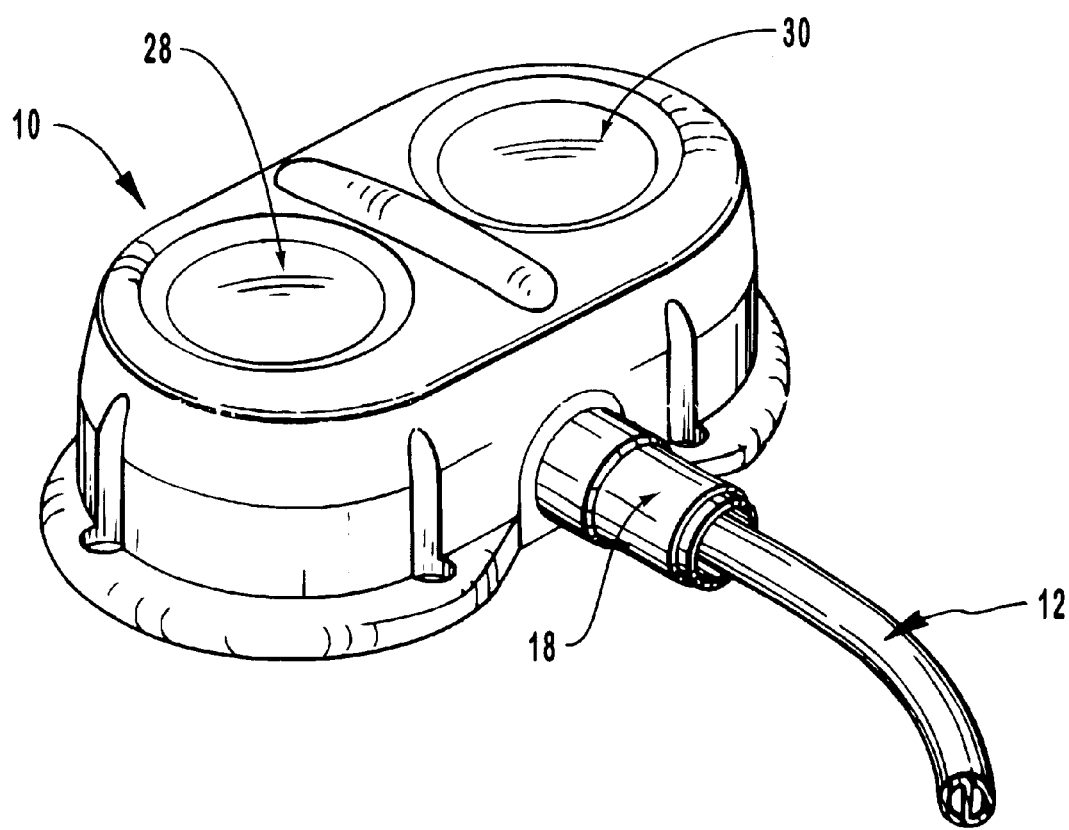
FIG. 1 is a perspective view of a known implantable vascular access system including a dual reservoir vascular access port and a dual lumen vascular access catheter.
Figure 2:
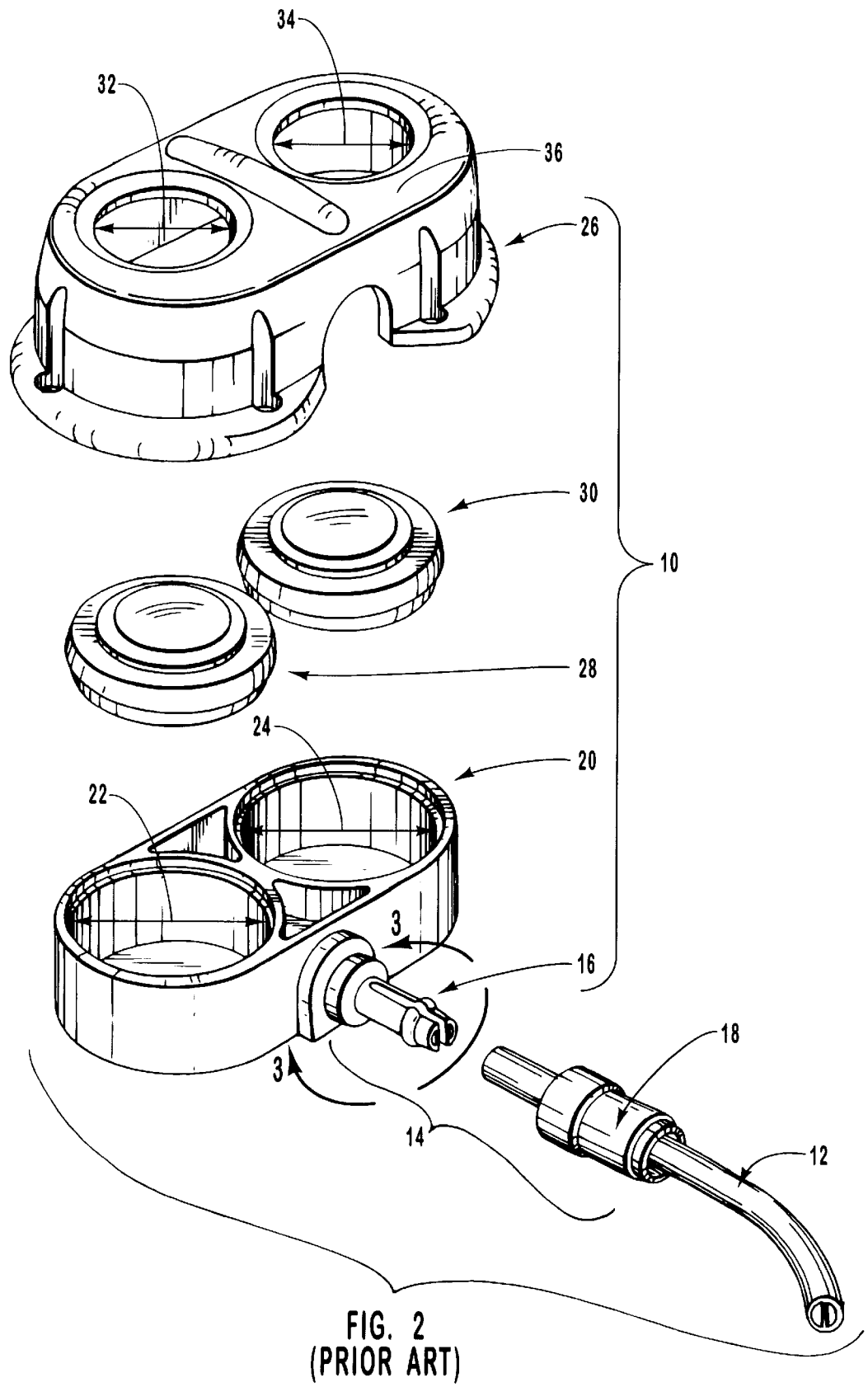
FIG. 2 is an exploded perspective view of the components of the known vascular access system of FIG. 1, which components, other than the elements of the catheter connection system utilized, include from the top to the bottom of the figure, a cap, a pair of septums, and a base having an outlet stem projecting therefrom.
Figure 3:
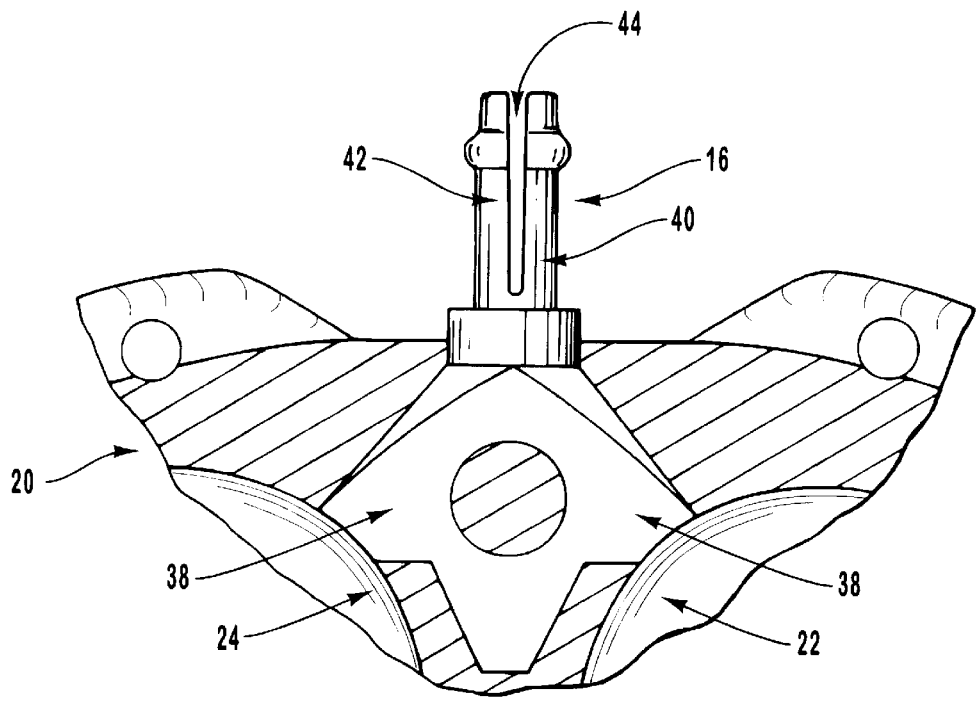
FIG. 3 is an enlarged plan view in partial breakaway of the portion of the base of FIG. 2 surrounding the outlet stem that projects therefrom.
Figure 4:
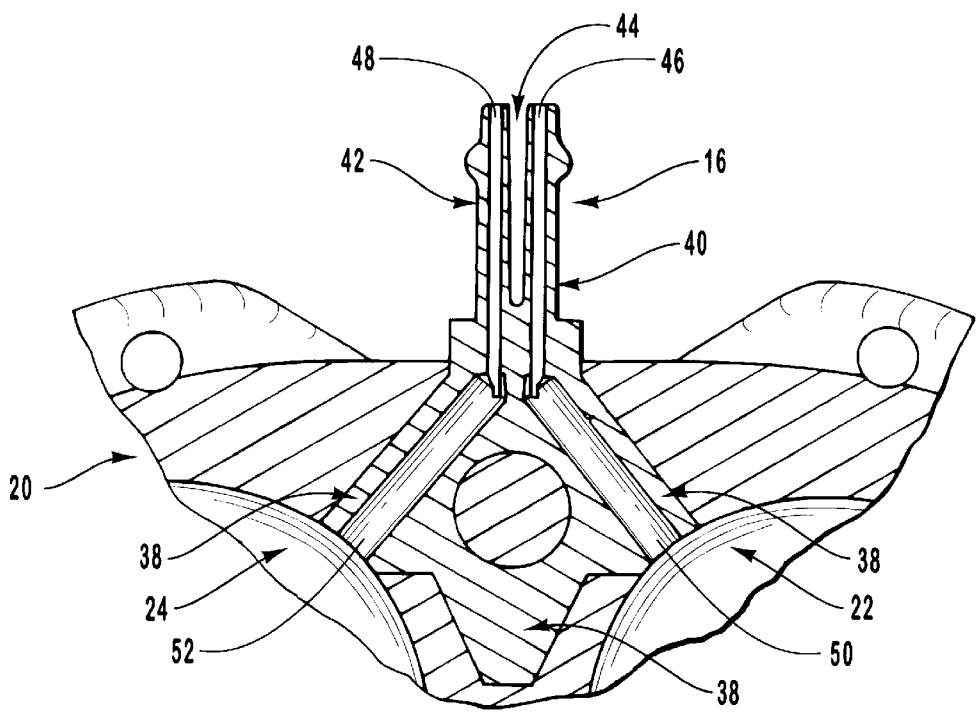
FIG. 4 is a cross-sectional plan view of the outlet stem of FIG. 3 and the portion of the base of FIG. 2 immediately adjacent thereto.
Figure 5:
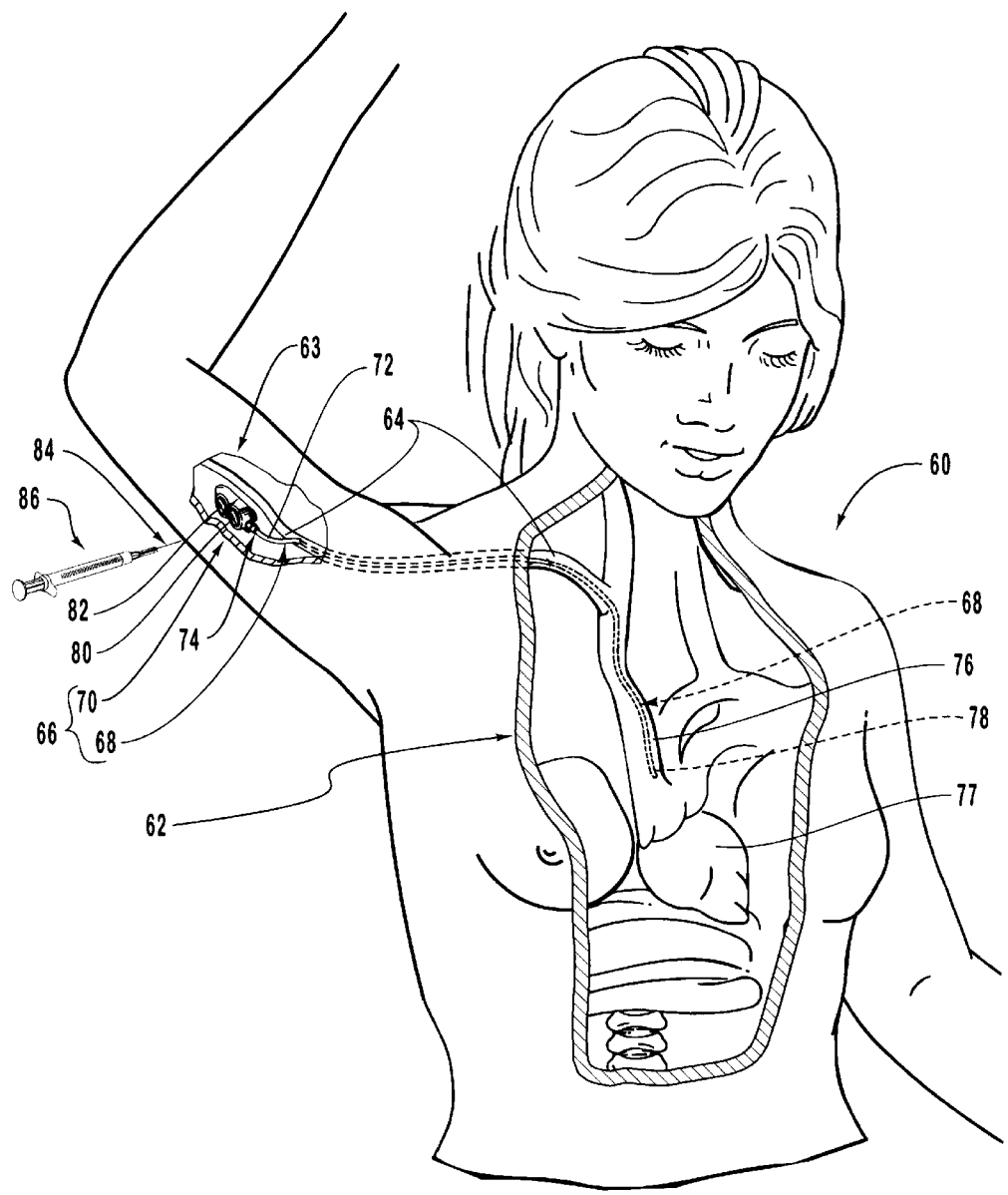
FIG. 5 is a perspective view of a first embodiment of an implantable vascular access system including a dual reservoir vascular access port incorporating teachings of the present invention attached to a dual lumen vascular access catheter and implanted in the body of a patient.

Referring to FIG. 5, a patient 60 is shown having a chest 62 and an upraised arm 63 in both of which a subclavian vein 64 appears. Implanted within arm 63 and chest 62 of patient 60 are substantially all of the elements of a vascular access system 66 that includes a vascular access catheter 68 and a vascular access port 70 incorporating teachings of the present invention.

Catheter 68 is made of a pliable material and has a proximal end 72 that is attached in fluid communication to vascular access port 70 using a catheter connection system 74 that will be revealed in additional detail subsequently. The role of catheter 68 in vascular access system 66 is to serve as a conduit for medication or other fluids between vascular access port 70 and a region of the cardiovascular system of patient 60 where immediate vigorous mixing with bodily fluids can promptly occur. Such a region can be found, among others, in the superior vena cava 76. Toward this end, catheter 68 extends subcutaneously in arm 63 to subclavian vein 64, where catheter 68 actually enters the cardiovascular system of patient 60. Distally therefrom, however, catheter 68 is advanced along subclavian vein 64 toward the heart 77 of patient 60, so that the distal end 78 of catheter 68 comes to be disposed in superior vena cava 76.

As vascular access port 70 is shown as including a first septum 80 and a second septum 82, vascular access port 70 is a dual reservoir vascular access port enclosing distinct fluid reservoirs therewithin. Correspondingly, catheter 68 is a dual lumen catheter. As thusly implanted, vascular access system 66 affords a medical practitioner ready access to a central, high-flow region of the cardiovascular system of patient 60 through the employment of a hypodermic needle 84 provided with a fluid syringe 86. The tip of hypodermic needle 84 is used to pierce the tissue of patient 60 at the implantation site for vascular access port 70. Then, the tip of hypodermic needle 84 is advanced through one of first septum 80 and second septum 82 into a corresponding fluid reservoir within vascular access port 70. Infusion or aspiration of fluids can then be effected through correspondingly operating fluid syringe 86 in a manner discussed previously.

Figure 6:
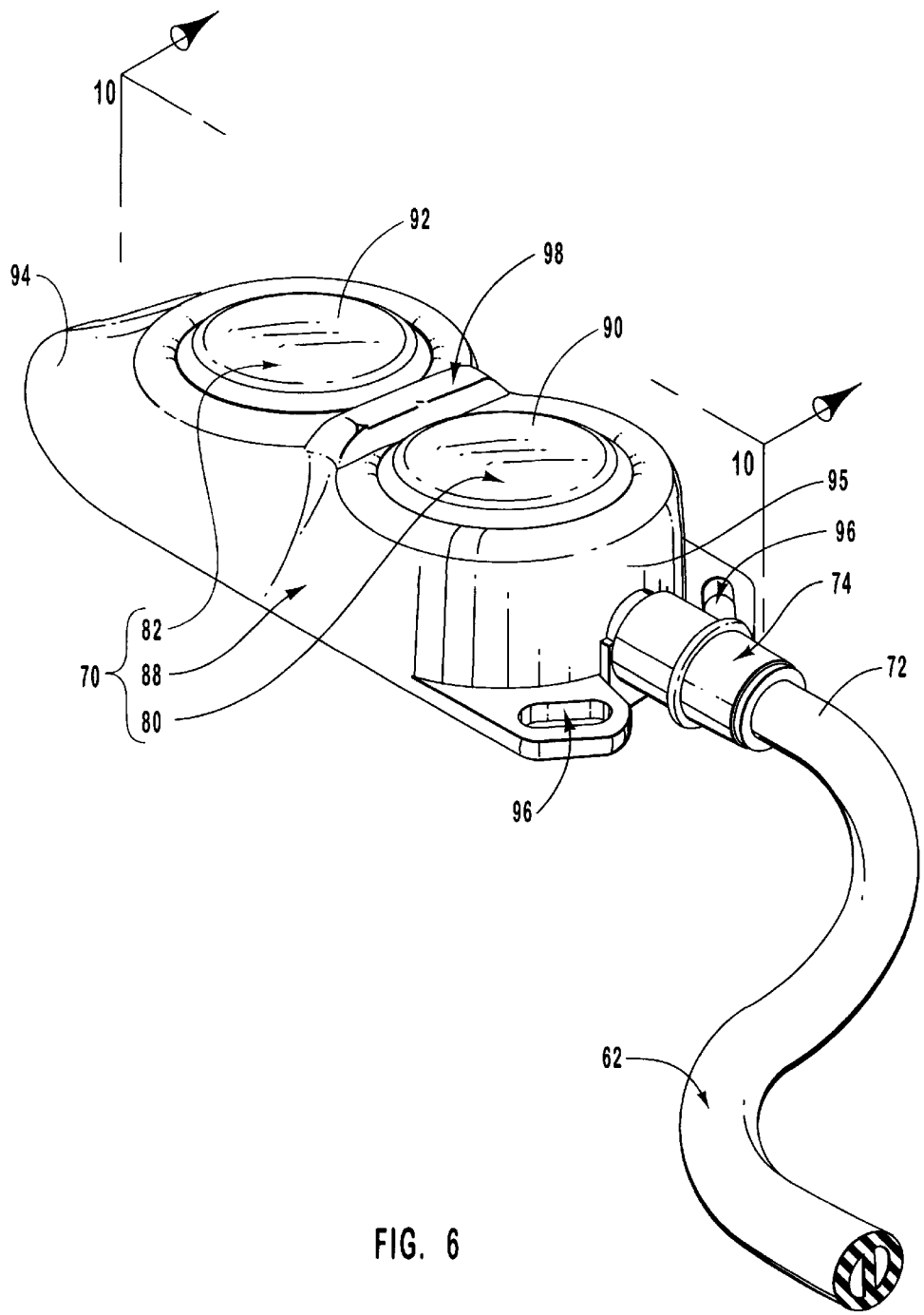
FIG. 6 is an enlarged perspective view of the vascular access port of FIG. 5 and the proximal end of the catheter attached thereto.

FIG. 6 provides an enlarged perspective view of vascular access port 70 of FIG. 5 and proximal end 72 of catheter 68 that is attached thereto by catheter connection system 74. As depicted in FIG. 6, vascular access port 70 includes a needle-impenetrable shell 88 that encloses a pair of distinct fluid reservoirs not visible in FIG. 6. Elastomeric needle-penetrable first septum 80 and elastomeric needle-penetrable second septum 82 afford for repeated selective access to the fluid reservoirs in shell 88 when penetrated by the tip of a hypodermic needle, such as hypodermic needle 84 shown in FIG. 5. The portion of first septum 80 exposed to the exterior of shell 88 is a slightly convex first target dome 90, while the corresponding portion of second septum 82 exposed to the exterior of shell 88 is a slightly convex second target dome 92.

By way of information, shell 88 of vascular access port 70 includes a tapered distal end 95 and opposite therefrom a proximal end 94 at which a pair of suture apertures 96 are formed. Using these structures, vascular access port 70 can be securely stabilized subcutaneously at the intended implantation site therefor. Between first target dome 90 of first septum 80 and second target dome 92 of second septum 82, shell 88 is provided with an elongated, raised tactile locating ridge 98 that facilitates the transcutaneous ascertainment by medical personnel of the precise subcutaneous location of each of first target dome 90 and second target dome 92. To do so, the body location at which vascular access port 70 is implanted is palpated first to locate vascular access port 70, and then to find tactile locating ridge 98.

Figure 7:
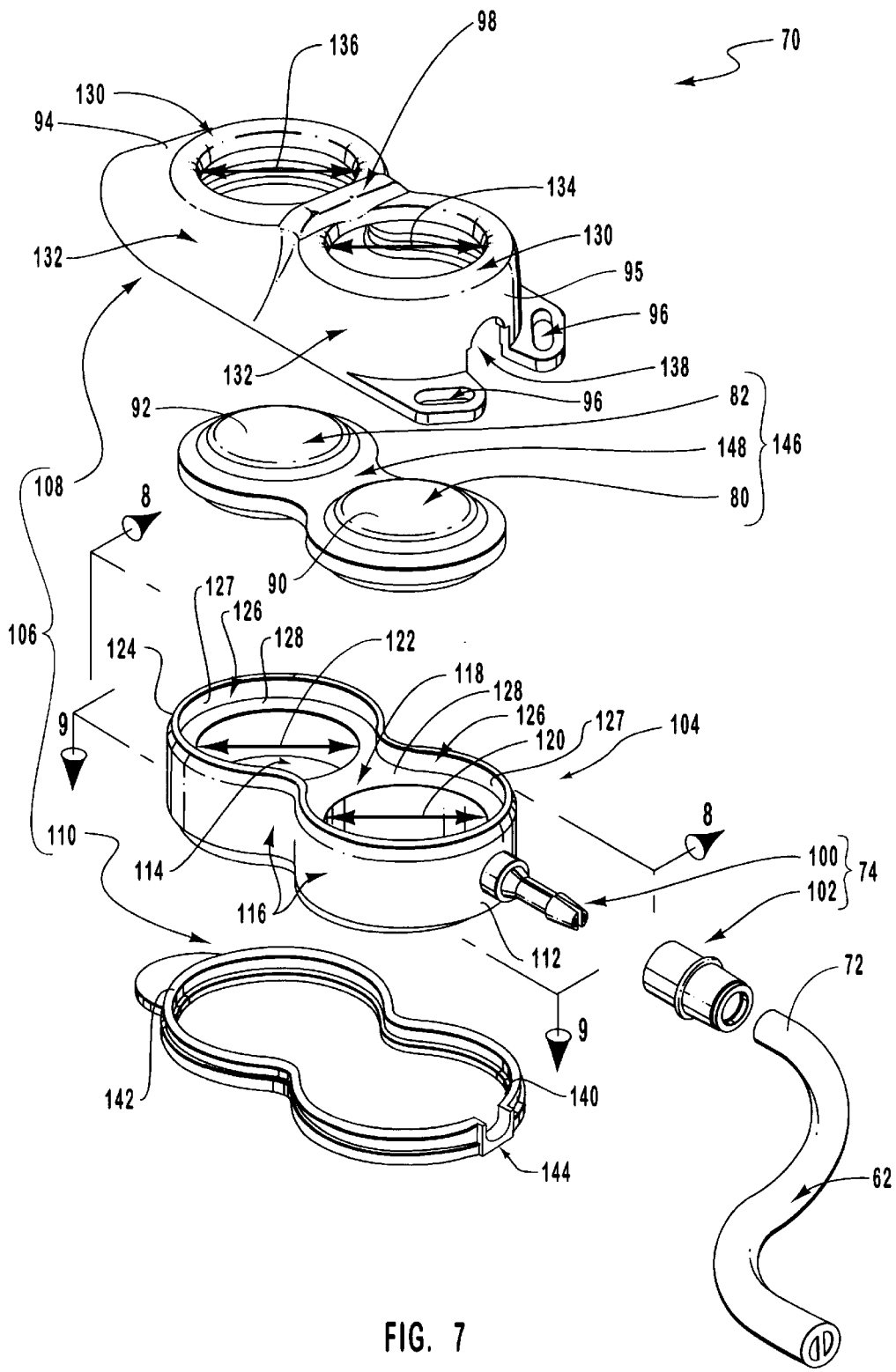
FIG. 7 is an exploded perspective view of the components of the vascular access system of FIG. 5, which components, other than the elements of the catheter connection system utilized, include from the top to the bottom of the figure, a cap, a compound septum, a housing having an outlet stem projecting therefrom, and a shoe.

As depicted in FIG. 7, shell 88 of vascular access port 70 shown in FIG. 6 includes an elongated housing 104 with outlet stem 100 and a two-piece clamp 106 that includes a cap 108 and a cooperating shoe 110. Housing 104 and outlet stem 100 are made of metal, while cap 108 and shoe 110 are both made of plastic.

Cap 108 and shoe 110 are configured for mating engagement to each other with housing 104 therebetween. In this manner, the elements of clamp 106 form the exterior surface of shell 88, while outlet stem 100 that is attached to distal end 112 of housing 104 projects through clamp 106 at proximal end 94 of shell 88 in the manner shown in FIG. 6.

Housing 104 includes a flat inner floor 114, an encircling sidewall 116 upstanding from and normal to inner floor 114, and an interior wall 118 also upstanding from and normal to inner floor 114. In this manner, sidewall 116 and interior wall 118 of housing 104 define therewithin a distal fluid reservoir 120 located in distal end 112 of housing 104, and a proximal fluid reservoir 122 located in proximal end 124 of housing 104. Upstanding from top surface 128 of encircling sidewall 116 at the outer edge of sidewall 116 is a continuous encircling lip 126 having an encircling inner surface 127 not shown in FIG. 7 and appearing in FIG. 8, that is oriented at each location thereon normal to the portion of top surface 128 of sidewall 116 adjacent thereto.

Cap 108 of clamp 106 is an elongated cup-like structure that comprises a top wall 130 with a skirt 132 that depends therefrom. Formed through top wall 130 of cap 108 is a distal access aperture 134 and a proximal access aperture 136. At an edge of skirt 132 remote from top wall 130 but between suture apertures 96 skirt 132 is interrupted by a stem receiving arch 138.

Shoe 110 is an open ring that assumes a figure-eight configuration and has a distal end 140 and a proximal end 142. Shoe 110 has, therefore, no floor whatsoever. At distal end 140 of shoe 110 a stem carriage 144 is provided that cooperates in the assembled state of vascular access port 70 with stem receiving arch 138 of cap 108 to afford access to the exterior of shell 88 for outlet stem 100.

FIG. 7 also reveals, however, that in vascular access port 70 first target dome 90 of first septum 80 and second target dome 92 of second septum 82 are actually portions of the outer surface of an integrally formed, needle-penetrable elastomeric article that will be referred to hereinafter as a compound septum 146. Typically, compound septum 146 is made of a resilient material, such as medical grade silicon. Compound septum 146 includes not only first septum 80 and second septum 82, but an interconnecting septum web 148 that encircles the periphery of both. In the assembled state of vascular access port 70, compound septum 146 is disposed against top surface 128 of sidewall 116 of housing 104, covering distal fluid reservoir 120 and proximal fluid reservoir 122.

Taken alone, FIG. 7 would tend to suggest that vascular access port 70 is comprised of only four (4) components: a needle-impenetrable housing, a single needle-penetrable compound septum, and two (2) needle-impenetrable clamp elements. This economy in components is, however, actually achieved by constructing housing 104 from three (3) separate elements, each made of metal. The structure of these components of housing 104 is better appreciated by reference to the cross-sectional views in FIGS. 8 and 9 taken together.

Figure 8:
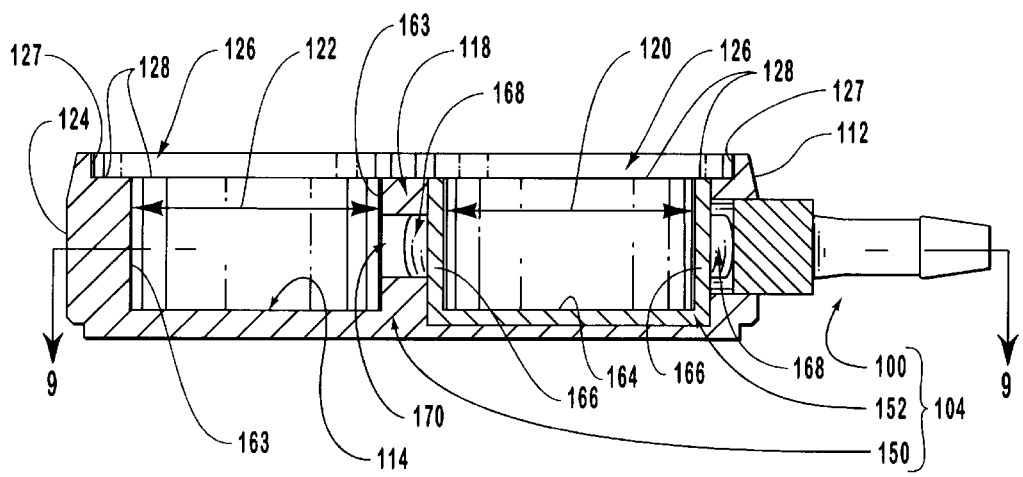
FIG. 8 is a cross-sectional elevation view of the housing of FIG. 7 taken along section line 8—8 shown therein.

As illustrated initially in FIG. 8, housing 104 comprises an elongated casing 150, an open-topped basket 152 that is received in casing 150, and outlet stem 100 that projects from casing 150 at distal end 112 of housing 104.

Figure 9:
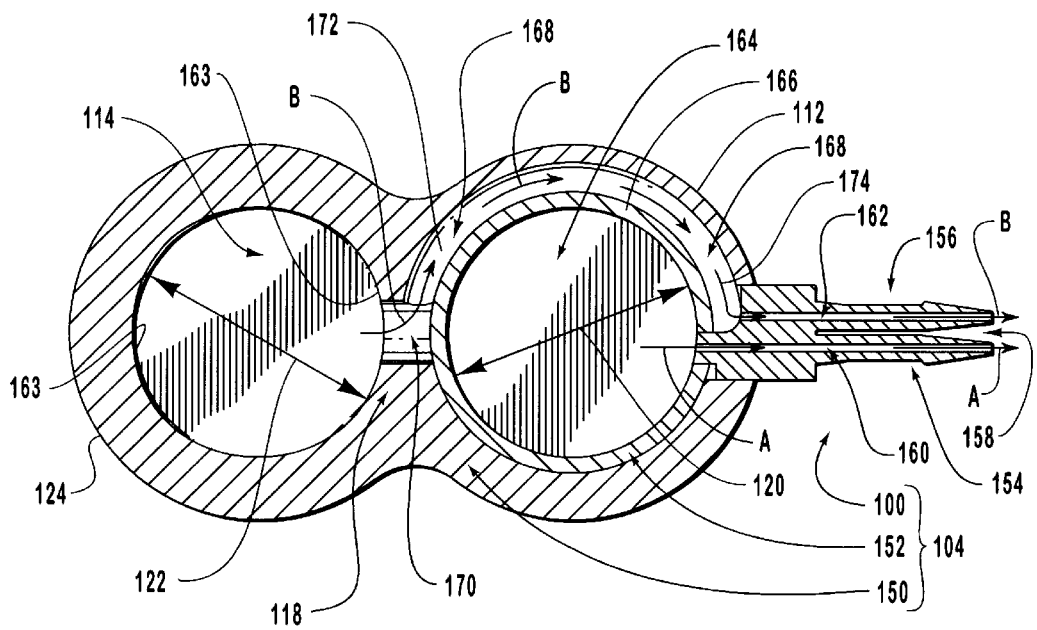
FIG. 9 is a cross-sectional plan view of the housing of FIGS. 7 and 8 taken along section line 9—9 shown in both.

FIG. 9 reveals that outlet stem 100 includes a pair of outlet prongs 154, 156 separated by an elongated slot 158. Fluid flow passageways 160, 162 are formed longitudinally within each of outlet prongs 154, 156, respectively. Fluid flow passageway 160 communicates directly with distal fluid reservoir 120 through encircling sidewall 166 of basket 152, thereby permitting the outward fluid flow from distal fluid reservoir 120, as shown by arrows A, in order to effect the infusion of medication or other fluids into the body of patient 60. Correspondingly, fluid flow in the opposite direction can occur to aspirate bodily fluids from the body of patient 60 through vascular access system 66.

Fluid flow passageway 162 by contrast communicates only indirectly with proximal fluid reservoir 122 through other intermediary structures in housing 104. An understanding of how this is achieved requires an exploration of additional structural aspects of housing 104 illustrated in FIG. 9, and to a degree in FIG. 8.

While proximal fluid reservoir 122 is formed directly in casing 150 of housing 104, distal fluid reservoir 120 is actually formed directly in basket 152. In assembling housing 104, basket 152 is in turn received in an appropriately configured recess in casing 150. Distal fluid reservoir 120 is defined by a planar lower floor 164 and an encircling sidewall 166 upstanding and normal thereto. The top of sidewall 166 is flush with top 128 of sidewall 166 of housing 104 once basket 152 has been received in casing 150.

A fluid conduit 168 is created between basket 152 and casing 150 by recessing a circumferentially extending elongated groove into a portion of the wall of the recess in casing 150 that receives basket 152. A transfer port 170 is formed through interior wall 118 of housing 104 at proximal end 172 of fluid conduit 168, thereby enabling fluid conduit 168 to communicate with proximal fluid reservoir 122. Distal end 174 of fluid conduit 168 communicates with fluid flow passageway 162 in outlet stem 100. In this manner, fluid flow passageway 162 in outlet stem 100 is able to communicate with proximal fluid reservoir 122 by way of fluid conduit 168 and transfer port 170, despite the positioning of proximal fluid reservoir 122 on the side of distal fluid reservoir 120 opposite from outlet stem 100. An outward fluid flow from proximal fluid reservoir 122 is then possible, as shown by arrows B in FIG. 9, in order to infuse medication or other fluids into the body of patient 60. Correspondingly, fluid flow in the opposite direction can occur to aspirate bodily fluids from the body of patient 60.

Figure 10:
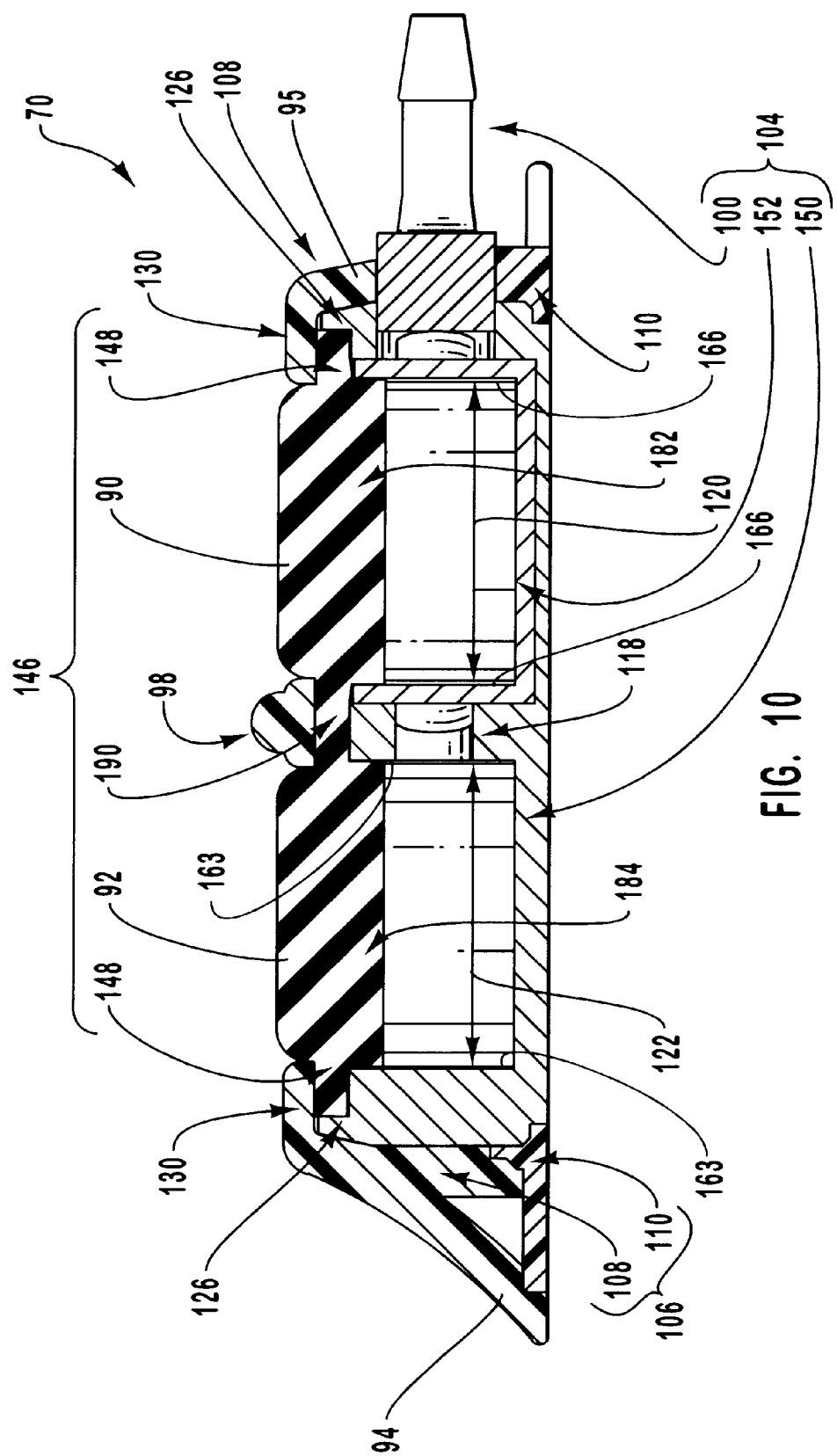
FIG. 10 is a cross-sectional elevation view of the assembled vascular access port of FIG. 6 taken along section line 10—10 shown therein.

FIG. 10 illustrates in cross section the assembled state of vascular access port 70. Distal access aperture 134 shown in the disassembled state of vascular access port 70 in FIG. 7 is disposed above distal fluid reservoir 120. Similarly, proximal access aperture 136 is disposed above proximal fluid reservoir 122. Compound septum 146 rests between cap 108 and housing 104 covering distal fluid reservoir 120 and proximal fluid reservoir 122 with first target dome 90 projecting through distal access aperture 134 to the exterior of vascular access port 70 and second target dome 92 projecting through proximal access aperture 136 to the exterior of vascular access port 70. Compound septum 146 is compressed and secured in this sealing engagement with housing 104 by the cooperating action of the elements of clamp 106 to either side of compound septum 146 and housing 104.

One noteworthy feature of vascular access port 70 is the use of a single needle-penetrable elastomeric article to seal each of the distinct fluid flow reservoirs within vascular access port 70 simultaneously. While compound septum 146 not only precludes the transfer of fluids between the exterior of vascular access port 70 and either of distal fluid reservoir 120 and proximal fluid reservoir 122, compound septum 146 also prevents the passage of fluid between distal fluid reservoir 120 and proximal fluid reservoir 122.

The integrated structure of compound septum 146 reduces the number of parts required in the assembly of vascular access port 70, and also produces an economy in the overall size of vascular access port 70 relative to dual reservoir vascular access ports that employ a pair of individual septums. For example, using compound septum 146, the fluid seal between distal fluid reservoir 120 and proximal fluid reservoir 122 is effected using the same portioned septum for compound septum 146, namely a central region 190 of septum web 148 that is disposed between distal fluid reservoir 120 and proximal fluid reservoir 122, when vascular access port 70 is assembled. This correspondingly reduces the size of the portion of housing 104 of vascular access port 70 that must be included to engage septum material between distal fluid reservoir 120 and proximal fluid reservoir 122. As a result, distal fluid reservoir 120 and proximal fluid reservoir 122 can be positioned closely together in housing 104, decreasing the overall size of housing 104.

Figure 11:
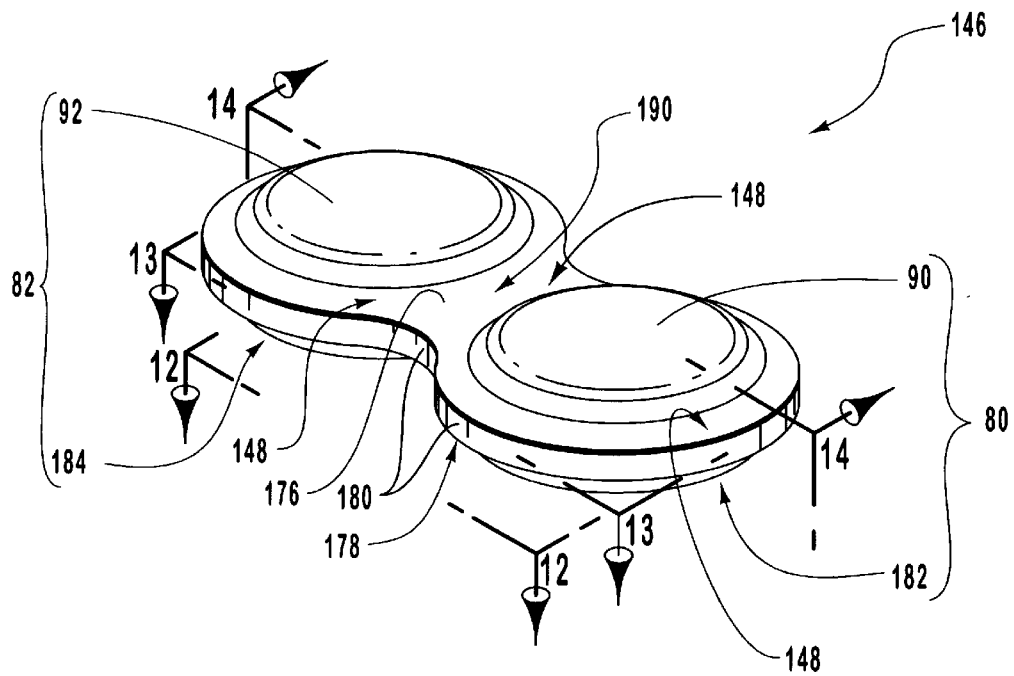
FIG. 11 is an enlarged perspective view of the compound septum of FIG. 7.

In view of the significance of compound septum 146, a closer exploration of the structure thereof will be undertaken in relation to FIG. 11. There, septum web 148 of compound septum 146 can be seen to be a planar structure having a top surface 176, a bottom surface 178 parallel thereto, and a continuous side surface 180 extending between top surface 176 and bottom surface 178. First target dome 90 and second target dome 92 project from top surface 176 of septum web 148, but corresponding structures also project from bottom surface 178. These are a first septum plug 182 and a second septum plug 184. First septum plug 182 projects from bottom surface 178 of septum web 148 at a location directly opposite first target dome 90. First target dome 90 and first septum plug 1 82 together function as first septum 80. Second septum plug 184 also projects from bottom surface 178 of septum web 148, but at a location that is directly opposite from second target dome 92. Accordingly, second septum plug 184 and second target dome 92 together function as second septum 82.

Compound septum 146 is configured to have specific desirable properties in the installed configuration thereof when assembled in vascular access port 70. For example, when the tip of a hypodermic needle penetrates either first septum 80 or second septum 82 of compound septum 146, these components of compound septum 146 should seal around the exterior of the shaft of the hypodermic needle and prevent the passage of fluid to or from the fluid reservoir being accessed. In addition, compound septum 146 is configured in such a manner as to produce a predetermined amount of needle retention force on such a hypodermic needle. Needle retention force refers to the degree to which a septum resists the withdrawal from the septum of the shaft of a hypodermic needle that has penetrated through the septum.

The sealing effectiveness and the needle retention force associated with the installed configuration of compound septum 146 are in part related to the amount of radially inwardly directed force applied to compound septum 146 by housing 104. In general, the greater the force applied, the higher the sealing effectiveness and the needle retention force in the installed configuration of compound septum 146. Such applied forces actually deform compound septum 146, causing radially inwardly directed strain about side surface 180 of septum web 148 and about other elements of compound septum 146. This strain in turn alters the hydrostatic pressure existing throughout the material matrix of the installed configuration of compound septum 146, varying the sealing effectiveness and the needle retention force throughout.

Nonetheless, the degree of strain imposed on compound septum 146 must not be so great that penetrating either first septum 80 or second septum 82 in the installed configuration of compound septum 146 results in coring. Coring occurs when the hydrostatic pressure existing in the material of the installed configuration of a septum is so high that, when the tip of a hypodermic needle is advanced through the material of the septum, a portion of that material is forced inside the needle. That portion of the septum material forced inside the needle is, in effect, severed from the septum, resulting in a small, but nonetheless distinct, material discontinuity that may extend entirely through the septum. While the strain imposed on such an installed septum will initially tend to seal such material discontinuities, continued coring eventually results in septum failure.

Compound septum 146 should also be configured to exhibit properties of sealing and of needle retention in the areas thereof exposed for needle penetration that are substantially uniform. In the case of compound septum 146, these areas are defined by first target dome 90 and second target dome 92. When uniform properties of sealing and of needle retention can be effected in these regions of the installed configuration of a septum, the quality of the interactions between the septum and the tip of a penetrating hypodermic needle will be substantially independent of the location at which the tip of the hypodermic needle penetrates the septum.

Figure 12:
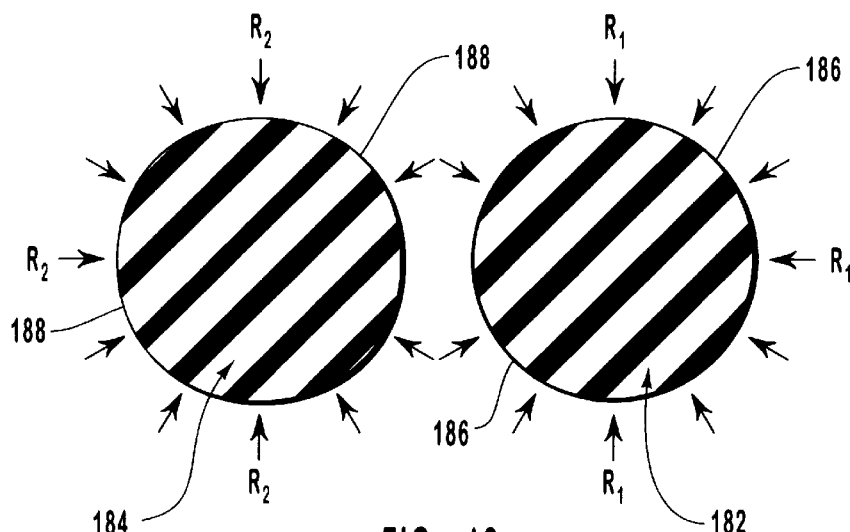
FIG. 12 is a cross-sectional plan view of the septum plugs of the compound septum of FIG. 11 taken along section line 12—12 shown therein.

To achieve these several objectives, first septum plug 182 has a perimeter 186 shown in FIG. 12 that is slightly larger than the perimeter of distal fluid reservoir 120 as defined by sidewall 166 of basket 152 as shown in FIG. 10. The resulting difference in sizes is sufficiently small to allow first septum plug 182 to be manually inserted into distal fluid reservoir 120, without causing buckling of first septum plug 182. As a result, however, radially inwardly directed uniform force is applied about perimeter 186 of first septum plug 182 by sidewall 166, and perimeter 186 is radially inwardly displaced uniformly. In the cross-section of FIG. 12, these radially inwardly directed forces on perimeter 186 of first septum plug 182 are designated by arrows $R_1$.

Second septum plug 184 has a similar size relationship to proximal fluid reservoir 122. Accordingly, as also depicted in FIG. 12, radially inwardly directed uniform forces $R_2$ are applied to perimeter 188 of second septum plug 184 by sidewall 163 of proximal fluid reservoir 122.

Figure 13:
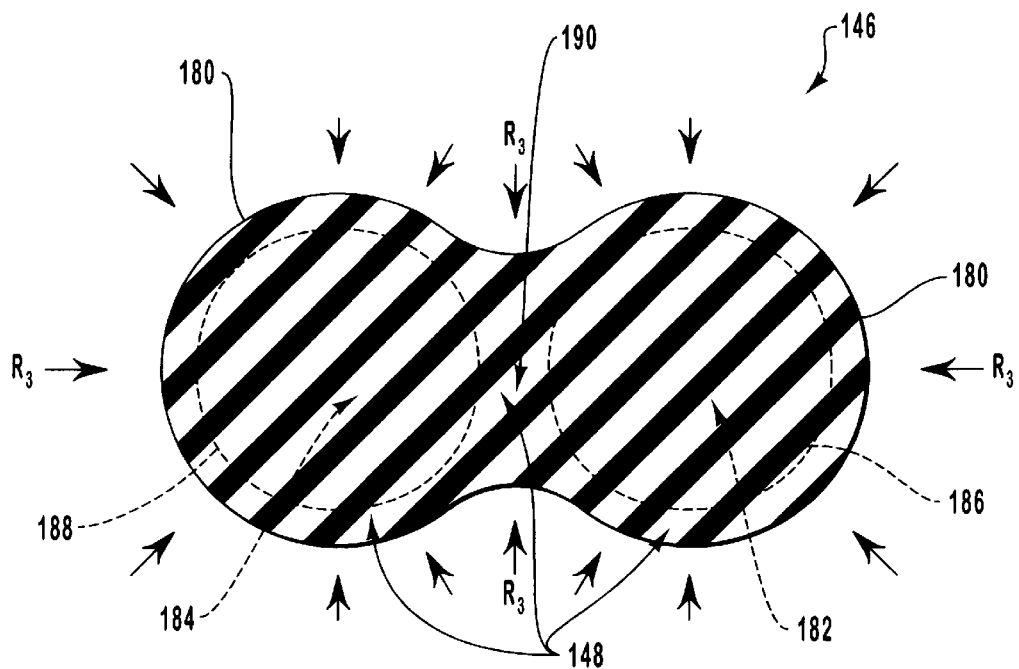
FIG. 13 is a cross-sectional plan view of the septum web of the compound septum of FIG. 11 taken along section line 13—13 shown therein.

Septum web 148 also has an outer perimeter defined by side surface 180 thereof. Inner surface 127 of lip 126 of housing 104 correspondingly defines the perimeter of a region in housing 104 that is intended to receive septum web 148. The exterior perimeter of septum web 148 is, however, larger than inner surface 127 of lip 126 of housing 104. The difference in perimeter sizes is sufficiently small to allow septum web 148 to be disposed manually in lip 126 without causing buckling in compound septum 146, As a result, inner surface 127 of lip 126 of housing 104 imposes radially inwardly directed forces to side surface 180 of septum web 148 that are represented in FIG. 13 by arrows $R_3$. Forces $R_3$ in turn radially inwardly displace side surface 180 of septum web 148 to a relatively uniform extent.

Nonetheless, due to the interaction of first septum plug 182 with sidewall 166 at distal fluid reservoir 120 and the interaction of second septum plug 184 with sidewall 163 of proximal fluid reservoir 122, the hydrostatic pressures produced by forces $R_3$ in the material matrix of septum web 148 in the installed condition of compound septum 146 are not uniform. Particularly problematic is an area of low level hydrostatic pressure developed in central region 190 of septum web 148 between first septum plug 182 and second septum plug 184. To remedy this lack of uniformity in the hydrostatic pressure produced, the thickness of septum web 148 as indicated by the height of side surface 180 thereof is greater than the height of lip 126 above top 128 of sidewall 116 of housing 104. When compound septum 146 is received within lip 126, side surface 180 of septum web 148 accordingly extends above the top of lip 126.

Figure 14:
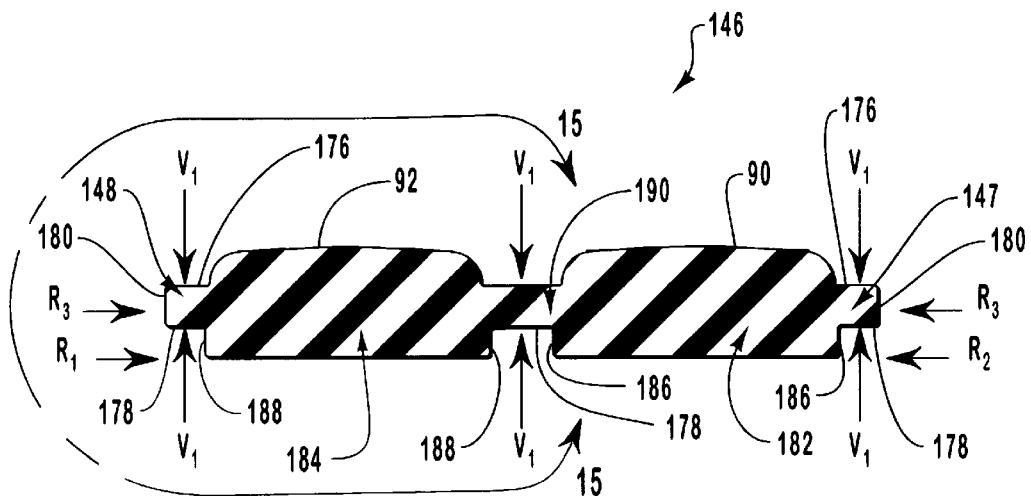
FIG. 14 is a cross-sectional elevation view of the compound septum shown in FIG. 11 taken along section line 14—14 shown therein.

To assemble the components of vascular access port 70 compound septum 146 is manually installed within lip 126 of housing 104 with first septum plug 182 extending into distal fluid reservoir 120 and with second septum plug 184 extending into proximal fluid reservoir 122. Then the resulting sub-assembly of housing 104 and compound septum 146 is received in cap 108. Shoe 110 is aligned with cap 108 and attached thereto as shown in FIG. 10 using adhesive or an ultrasonic welding process. As a result, top surface 176 and bottom surface 178 of septum web 148 are displaced axially towards each other by cap 108 and housing 104, respectively. This results in the application to septum web 148 of axially-directed forces $V_1$ illustrated in FIG. 14.

Figure 15:
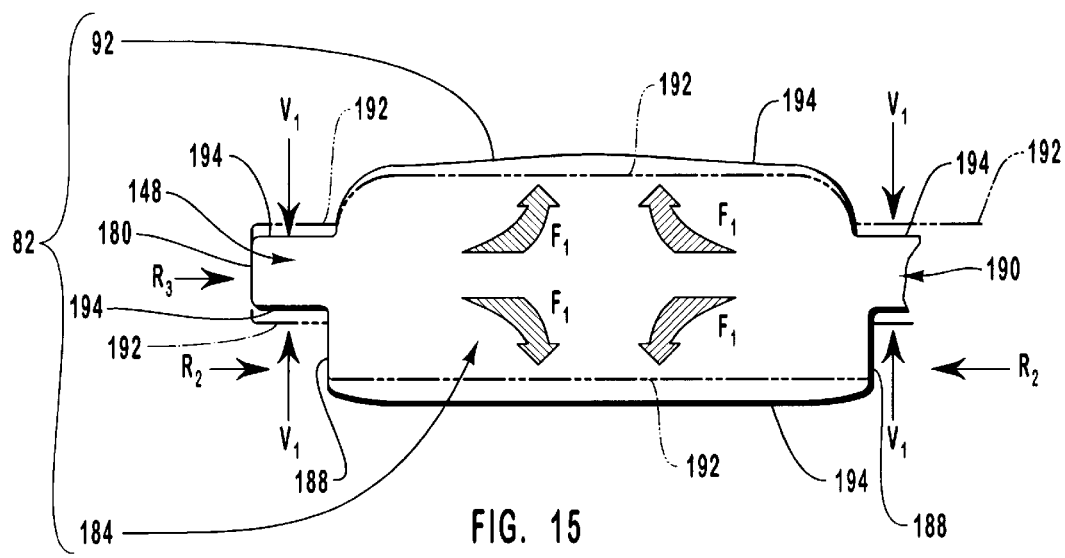
FIG. 15 is a diagram containing superimposed comparative elevation profile views of one side of the compound septum of FIG. 14 in the natural condition thereof shown in phantom and in the installed configuration thereof as in FIG. 10 shown in solid line.

In FIG. 15, a profile of the natural configuration 192 of compound septum 146 is shown in phantom, free from the effect of any axially-directed forces, such as axially-directed forces $V_1$. By way of contrast, a profile of the installed configuration 194 of compound septum 146 that results from the application of axially-directed forces $V_1$ is shown in solid line. For simplicity only second septum 82 and the portions of septum web 148 adjacent thereto are shown.

As shown in FIG. 15, when axially-directed forces $V_1$ are applied to septum web 148, the thickness of septum web 148 is decreased. Correspondingly, a portion of the material of compound septum 146 is urged radially inwardly into second septum 82, as represented by arrows $F_1$. A similar displacement of material occurs relative to first septum 80 now shown. The displacement of materials represented by arrows $F_1$ into the remaining portions of compound septum 146 causes an increase in the thickness of those regions, as is also shown in FIG. 15, but relative to second septum 82 only. Axially-directed forces $V_1$ that tend to displace toward each other top surface 176 and bottom surface 178 of septum web 148 are thus converted in part to horizontal forces that tend to increase the hydrostatic pressure otherwise developed in first target dome 90 and first septum plug 182 of first septum 80, as well as in second target dome 92 and second septum plug 184 of second septum 82.

The combination of the forces described above as being applied to compound septum 146 result in first septum 80 sealing distal access aperture 134 and second septum 82 sealing proximal access aperture 136. These forces also cause the development of uniform hydrostatic pressure in the portions of compound septum 146 likely to be penetrated by the tip of a hypodermic needle. This in turn results in uniform sealing and needle retention properties in those portions of compound septum 146.

Figure 16:
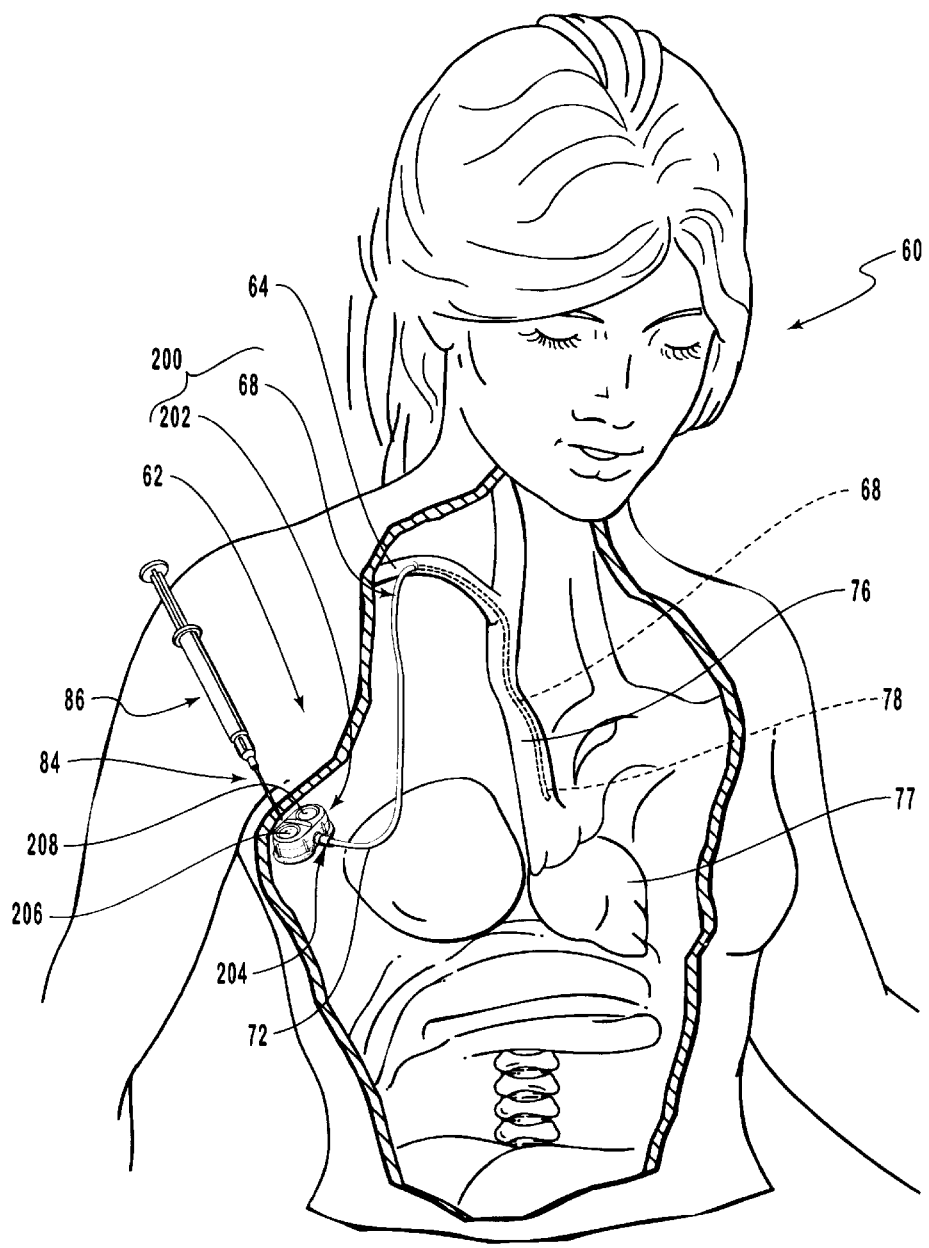
FIG. 16 is a perspective view of a second implantable vascular access system that includes an alternative embodiment of a dual reservoir vascular access port incorporating teachings of the present invention attached to a dual lumen vascular access catheter and implanted in the body of a patient.

An implantable second vascular access system 200 that includes an alternative embodiment of dual reservoir vascular access port incorporating teachings of the present invention is illustrated commencing with FIG. 16.

There, patient 60 from FIG. 5 is again shown. Implanted within chest 62 of patient 60 are substantially all of the elements of a second vascular access system 200 that includes a vascular access catheter 68 and an alternative embodiment of a vascular access port 202 incorporating teachings of the present invention. A catheter connection system 204 that will be revealed in additional detail subsequently is used to attach proximal end 72 of catheter 68 to vascular access port 202. Catheter 68 extends therefrom subcutaneously to subclavian vein 64, where catheter 68 actually enters the cardiovascular system of patient 60. As shown, distal end 78 of catheter 68 is advanced along subclavian vein 64 toward heart 77 of patient 60, so as to be disposed in superior vena cava 76.

Vascular access port 202 is shown as including a first septum 206 and a second septum 208. Therefore, vascular access port 202 is a dual reservoir vascular access port enclosing distinct fluid reservoirs therewithin, and catheter 68 is a dual lumen catheter. As thusly implanted, second vascular access system 200 affords a medical practitioner access, using the tip of a hypodermic needle 84, to either of the fluid reservoirs in vascular access port 202.

Figure 17:
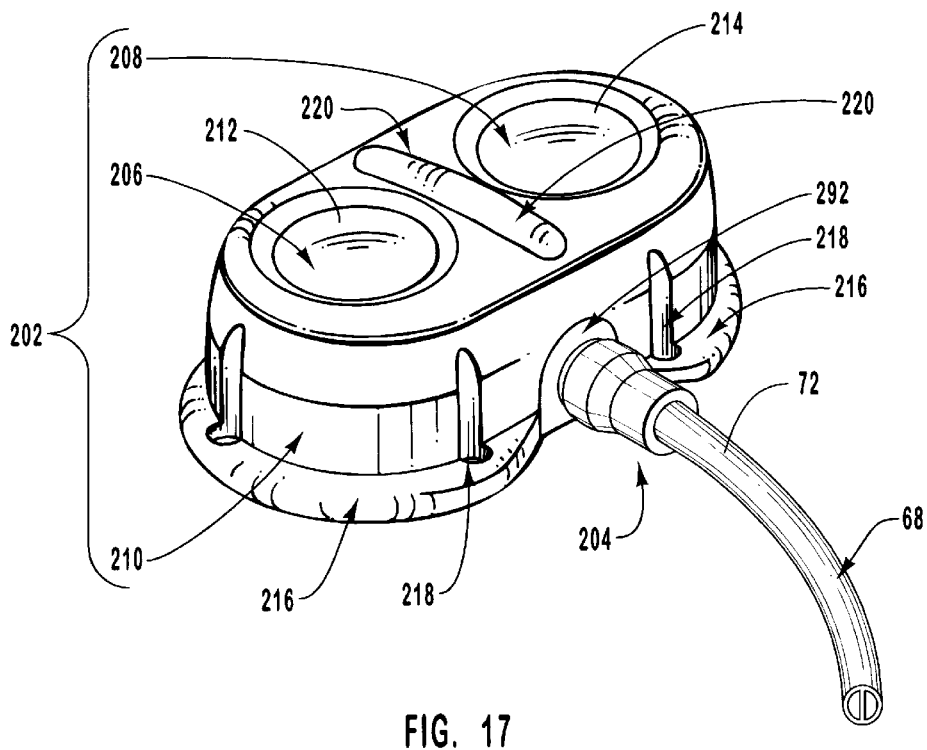
FIG. 17 is an enlarged perspective view of the vascular access port of FIG. 16 and the proximal end of the catheter attached thereto.

FIG. 17 provides an enlarged perspective view of vascular access port 202 of FIG. 16 and proximal end 72 of catheter 68 that is attached thereto by catheter connection system 204. There, vascular access port 202 can be seen to include a needle-impenetrable housing 210 that encloses a pair of distinct fluid reservoirs that are not visible in FIG. 17. Elastomeric needle-penetrable first septum 206 and elastomeric needle-penetrable second septum 208 afford for repeated selective access to the fluid reservoirs in housing 210 when penetrated by the tip of a hypodermic needle. The portion of first septum 206 exposed to the exterior of housing 210 is a slightly convex first target dome 212, while the corresponding portion of second septum 208 exposed to the exterior of housing 210 is a slightly convex second target dome 214.

By way of information, housing 210 of vascular access port 202 includes a suture ring 216 in which a plurality of suture apertures 218 is formed. Using these structures, vascular access port 202 can be securely stabilized subcutaneously at the intended implantation site therefor. Between first target dome 212 of first septum 206 and second target dome 214 of second septum 208, housing 210 is provided with an elongated, raised tactile locating ridge 220 that facilitates the use of vascular access port 202 in the manner of tactile locating ridge 98 of vascular access port 70 discussed earlier.

Figure 18:
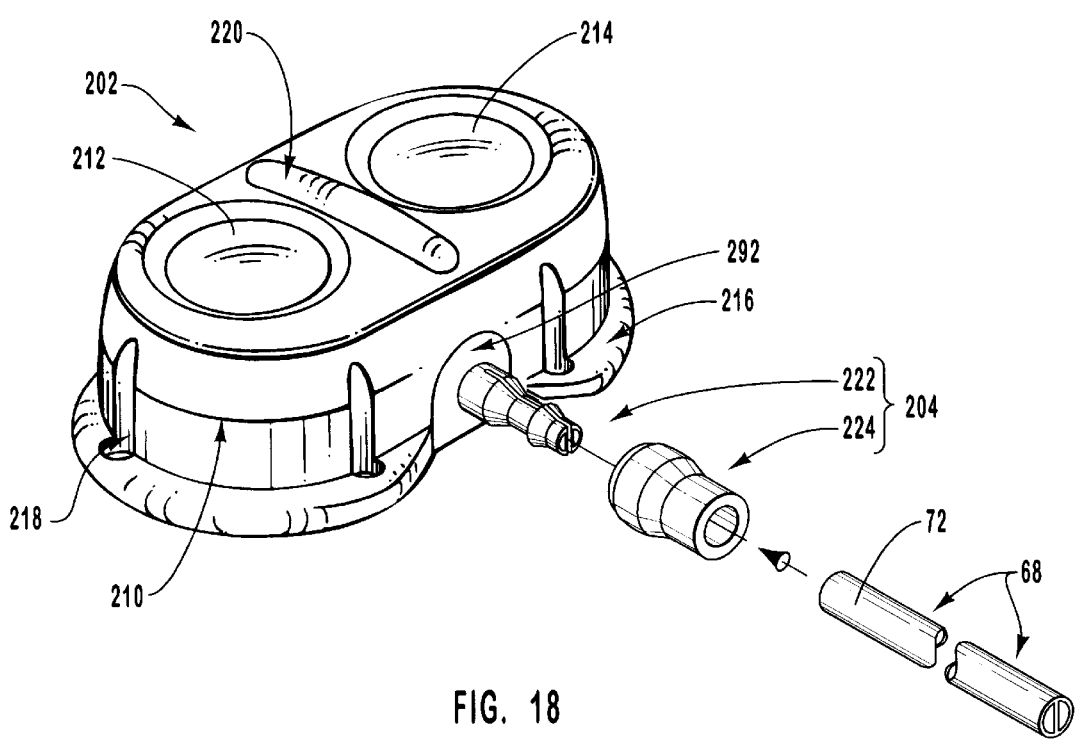
FIG. 18 is a perspective view of the vascular access port and catheter of FIG. 17 with the catheter detached from the vascular access port to reveal the elements of the catheter connection system utilized.

In FIG. 18, catheter 68 has been disengaged from vascular access port 202 to reveal the elements of catheter connection system 204 utilized. These elements include an outlet stem 222 that is received in the lumens of catheter 68 and a locking sleeve 224 that is freely slidable along the outer surface of catheter 68. To effect the coupling of proximal end 72 of catheter 68, proximal end 72 of catheter 68 is advanced longitudinally over the full length of outlet stem 222. Then, locking sleeve 224 is advanced along catheter 68 toward vascular access port 202 and urged onto the portion of proximal end 72 of catheter 68 in which outlet stem 222 has been received.

Figure 19:
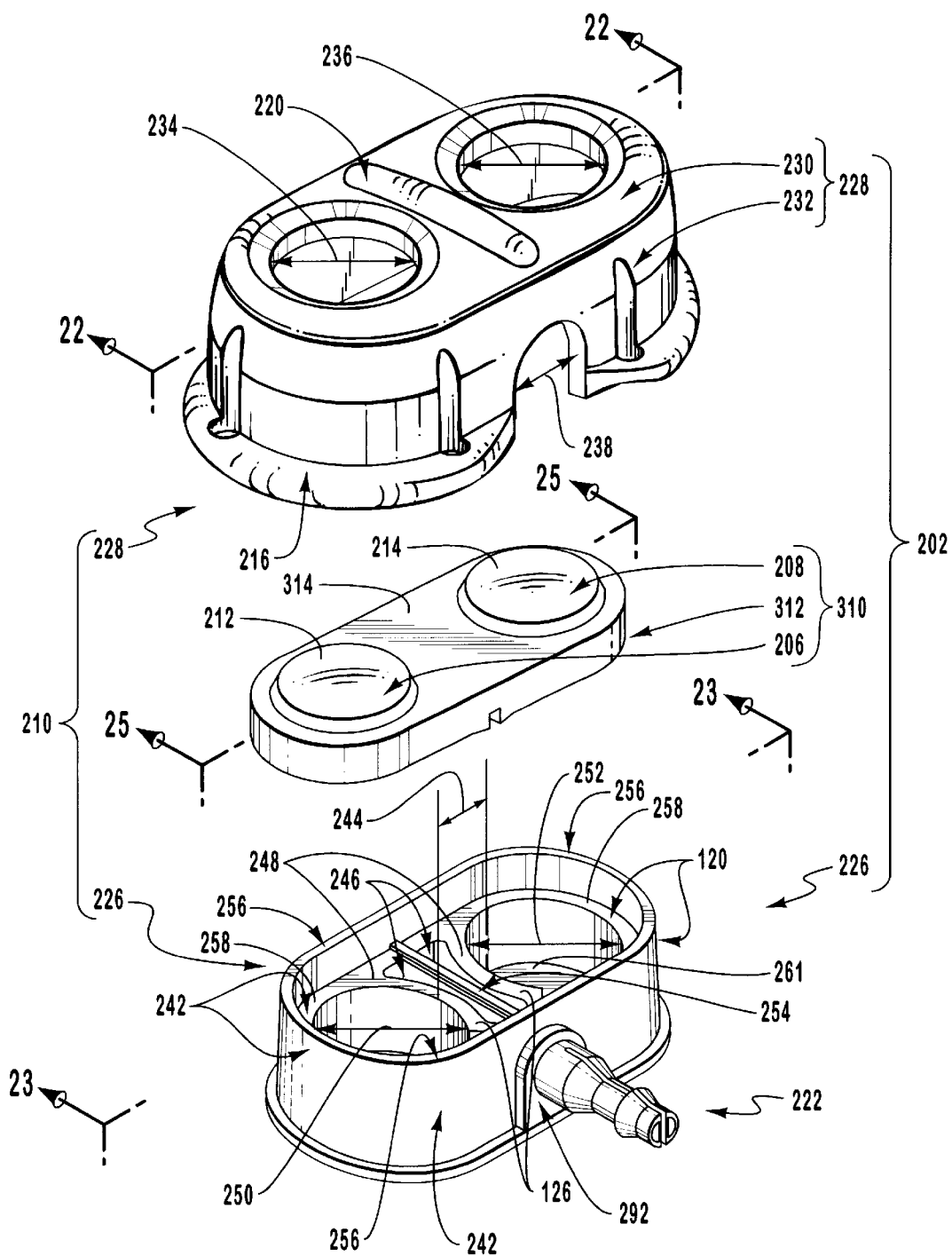
FIG. 19 is an exploded perspective view of the components of the vascular access port of FIG. 18, those components including from the top to the bottom of the figure, a cap, a compound septum, and a base having an outlet stem integrally formed therewith.

A better appreciation of the internal structure of vascular access port 202 can be obtained by reference to the exploded perspective view of the elements thereof appearing in FIG. 19. As depicted therein, housing 210 of vascular access port 202 actually includes two (2) components: an elongated needle-impenetrable base 226 and a correspondingly elongated needle-impenetrable cap 228 that is configured to receive base 226 therein.

Cap 228 is a cup-like structure that comprises a top wall 230 and an encircling skirt 232 that depends therefrom to terminate in suture ring 216. Formed through top wall 230 of cap 228 are a first access aperture 234 and a second access aperture 236. At an edge of skirt 232 remote from top wall 230 but intermediate first access aperture 234 and second access aperture 236, skirt 232 and suture ring 216 are interrupted by a stem receiving arch 238.

Figure 23:
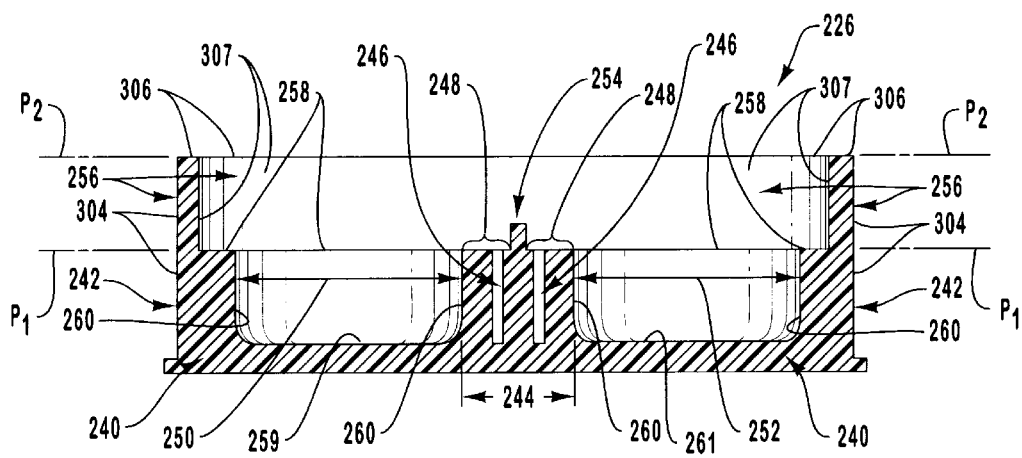
FIG. 23 is a cross-sectional elevation view of the base of FIGS. 19 and 20 taken along section line 23—23 shown in both.

Base 226 of housing 210 includes a flat bottom wall 240, shown in FIG. 23 an encircling sidewall 242 upstanding from and normal to bottom wall 240, and an interior wall 244 also upstanding from and normal to bottom wall 240 that interconnects a pair of nonadjacent locations on the interior of sidewall 242. To improve the efficiency of the injection molding process by which base 226 is fabricated, voids 246 are formed in interior wall 244 from top surface 248 thereof, giving interior wall 244 a three-layered appearance evident in FIG. 19.

In this manner, sidewall 242 and interior wall 244 of base 226 define therewithin a first fluid reservoir 250 on one side of interior wall 244 and a second fluid reservoir 252 on the other side of interior wall 244. A raised cloison 254 projects from top surface 248 of the central of the three layers of interior wall 244. Like interior wall 244, cloison 254 interconnects a pair of nonadjacent locations on the interior of encircling sidewall 242 of base 226. Finally, a continuous encircling lip 256 is upstanding from top surface 258 of encircling sidewall 242 at the outer edge thereof.

Figure 20:
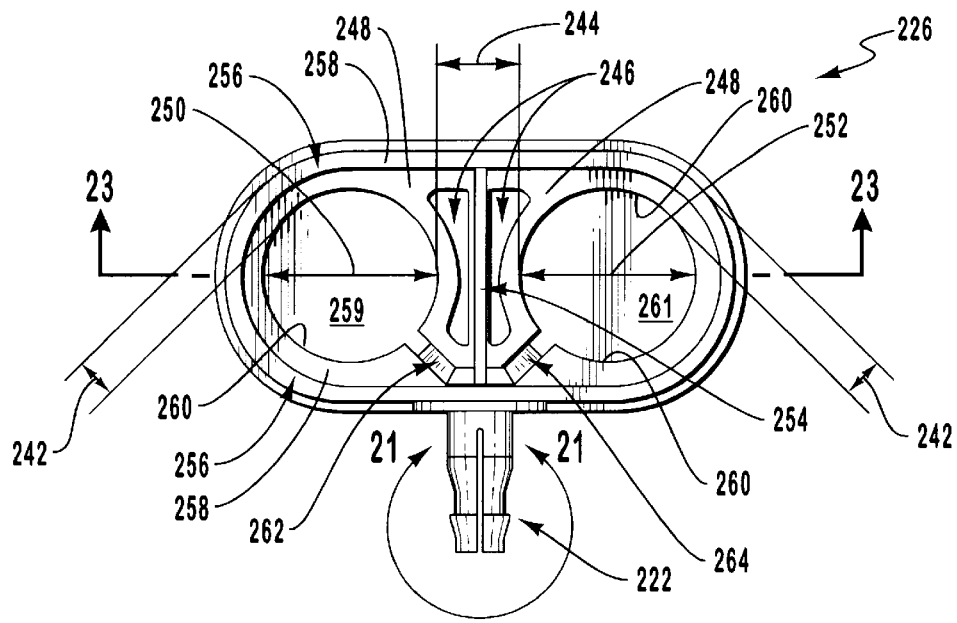
FIG. 20 is a plan view of the base of FIG. 19.

The relationships among these and yet additional elements of base 226 are discernable with additional clarity in the plan view of base 226 found in FIG. 20. There inner floor 259 of first fluid reservoir 250 and inner floor 261 of second fluid reservoir 252 appear in plan. The inner surfaces 260 that circumscribe each of first fluid reservoir 250 and second fluid reservoir 252 are seen on edge as circles.

Each of inner surfaces 260 is formed in part on the interior of sidewall 242 and in part on a side of interior wall 244, although any precise boundary between these two wall elements of base 226 can hardly be ascertained. Similarly, any boundary between top surface 258 of sidewall 242 and top surface 248 of interior wall 244 is unlikely to be precise.

Structures significant among the teachings of the present invention, but not visible in FIG. 19, are illustrated to better advantage in FIG. 20. These are an open-topped first fluid channel 262 and an open-topped second fluid channel 264. Each is an elongated recess in top surfaces 248 and 258 interior of lip 256. First fluid channel 262 communicates at one end thereof with first fluid reservoir 250, while second fluid channel 264 communicates at one end thereof with second fluid reservoir 252. First fluid channel 262 has parallel sides that are normal to inner floor 259 of first fluid reservoir 250. Likewise, second fluid channel 264 has parallel sides that are normal to inner floor 261 of second fluid reservoir 252. First fluid channel 262 communicates with first fluid reservoir 250 through a straight-sided first slot 263 that extends from top surfaces 248 and 258 into base 226 to the level of inner floor 259 of first fluid reservoir 250. Second fluid channel 264 communicates with second fluid reservoir 252 through a second slot 265 that extends from top surfaces 248 and 258 into base 226 to the level of inner floor 261 of second fluid reservoir 252.

Figure 21:
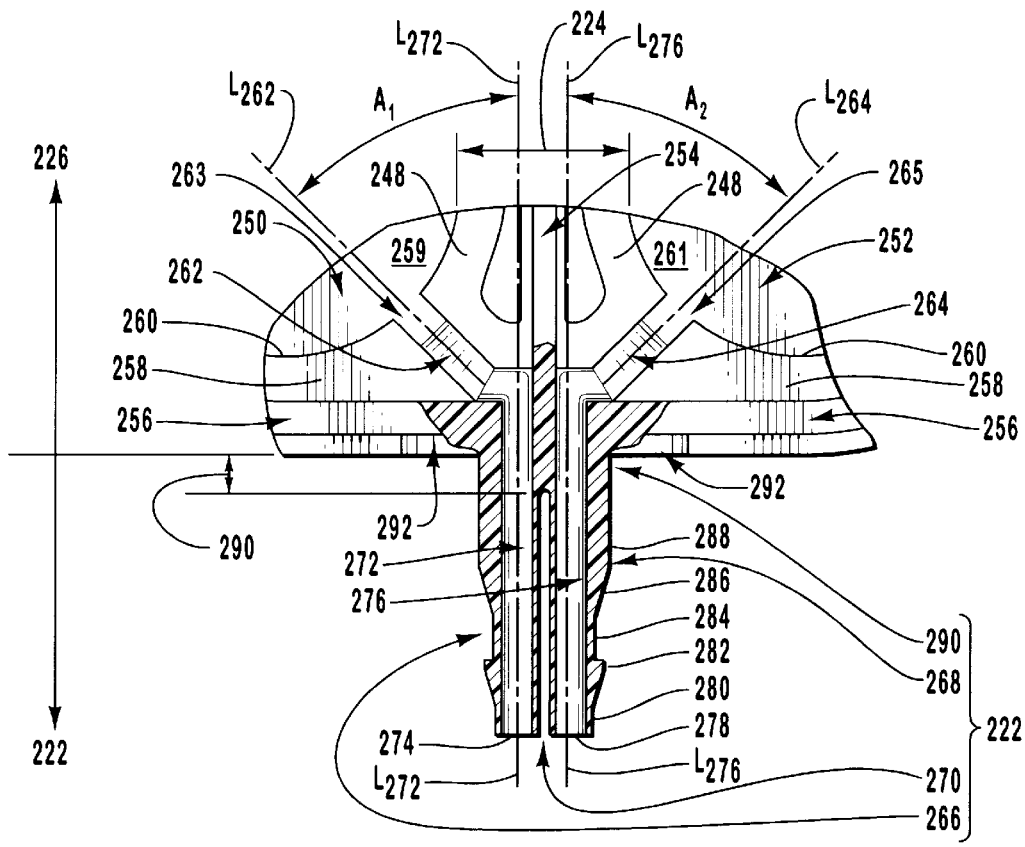
FIG. 21 is an enlarged plan view in partial breakaway of the outlet stem of FIG. 20 and the portion of the base immediately adjacent thereto.

Details of the structure of first fluid channel 262 and second fluid channel 264, as well as the relationship of each to the interior structure of outlet stem 222, can be discussed with enhanced clarity relative to the enlarged plan view of base 226 of housing 210 of vascular access port 202 shown in partial breakaway in FIG. 21. Outlet stem 222 and the portion of lip 256 of base 226 immediately adjacent thereto are shown in section, while the region of base 226 interior of lip 256 is, as in FIG. 20, shown in plan. FIG. 21 makes clear that outlet stem 222 is integrally formed with base 226 in such a manner as to project outwardly from sidewall 242 thereof. Therefore, base 226 is a single unitary component of vascular access port 202.

From the depiction of vascular access port 202 shown in FIG. 19, it can be observed that the design embodied in vascular access port 202 advantageously eliminates the use of any metal component whatsoever, even the metal outlet stem previously employed with many dual reservoir access ports. The entirety of vascular access port 202 can thus be fabricated from materials that are readily moldable, such as plastic from which base 226 and cap 228 are fabricated, or silicone from which compound septum 310 is formed. Neither of these materials requires the machining necessary to shape previous metal components. Correspondingly, the number of individual components in the design embodied in vascular access port 202 has been reduced to merely three: a pair of plastic housing components and a single compound septum.

Outlet stem 222 includes a first prong 266 and a second prong 268 disposed parallel to and separated from first prong 266 by an elongated slot 270. An enclosed first fluid passageway 272 extends longitudinally through first prong 266 from the free distal end 274 thereof to the interior of base 226 within lip 256. Similarly, an enclosed second fluid passageway 276 extends longitudinally through second prong 268 from free distal end 278 thereof to the interior of base 226 within lip 256. As a result of the parallel and adjacent disposition of first prong 266 and second prong 268, first fluid passageway 272 and second fluid passageway 276 can be characterized as extending longitudinally in a side-by-side relationship through outlet stem 222.

Advantageously, due primarily to the formation of first fluid channel 262 and second fluid channel 264 as open-topped recesses, it is possible to manufacture base 226 of housing 210 of vascular access port 202 in a single injection molding process. The design of base 226 illustrated includes no undercuts interior of lip 256. Enclosed first fluid passageway 272 and enclosed second fluid passageway 276 in outlet stem 222 are maintained as voids that communicate with first fluid channel 262 and second fluid channel 264, respectively, utilizing removable mandrel pins having cross sections conforming to the desired internal cross section of enclosed first and second fluid passageways 272 and 276. One such mandrel pin is inserted into the interior of the space in the mold in which base 226 is formed through a correspondingly cross-sectioned aperture in the wall of the mold cavity corresponding to free distal end 274 of first prong 266 of outlet stem 222. The other mandrel pin is inserted through a correspondingly cross-sectioned aperture in the wall of the mold cavity located at the portion thereof corresponding to free distal end 278 of second prong 268 of outlet stem 222.

As illustrated in FIG. 21, first fluid channel 262 has a longitudinal axis $L_{262}$ that forms an acute angle $A_1$ with the longitudinal axis $L_{272}$ of first fluid passageway 272 proximal of outlet stem 222 in the interior of base 226. Correspondingly, second fluid channel 264 has a longitudinal axis $L_{264}$ that forms an acute angle $A_2$ with longitudinal axis $L_{276}$ of second fluid passageway 276 proximal of outlet stem 222 in the interior of base 226. As illustrated, the size of acute angle $A_1$ is equal to the size of acute angle $A_2$, although such a relationship need not exist, if the symmetry of base 226 on either side of elongated slot 270 is not a concern. When acute angle $A_1$ is equal to about 45°, longitudinal axis $L_{262}$ of first fluid channel 262 passes through or close to the center of first fluid reservoir 250. A similar relationship will result relative to longitudinal axis $L_{264}$ and second fluid reservoir 252, if acute angle $A_2$ is equal to about 45°.

The exterior of each of first prong 266 and second prong 268 is identical. Only those structures on the exterior of second prong 268 will accordingly be discussed, but it should be noted that currently an outlet stem, such as outlet stem 222, is most optimally adapted for use with a 12 French dual lumen vascular access catheter made of soft medical grade silicone.

Progressing from free distal end 278 of second prong 268 toward base 226 of housing 210, the exterior of second prong 268 includes first a semi-cylindrical distal end portion 280, then a relatively sharp-shouldered barb 282, thereafter a semi-cylindrical medial portion 284, subsequently a tapered enlarging portion 286, and finally a semi-cylindrical proximal portion 288 of relatively large diameter. Between the closed end of elongated slot 270 and the exterior of sidewall 242 of base 226, semi-cylindrical proximal portions 288 of first prong 266 and second prong 268 merge into a single unified cylindrical base 290 for outlet stem 222. Cylindrical base 290 of outlet stem 222 is joined with base 226 of housing 210 at a shoulder 292 on the exterior of sidewall 242. In the assembled state of vascular access port 202 shown in FIG. 19 shoulder 292 is fitted into stem receiving arch 238 in skirt 232 of cap 228.

The internal features of the components of housing 210 of vascular access port 202 will be discussed in greater detail below with reference to the cross-sectional views presented in FIGS. 22—24.

Figure 22:
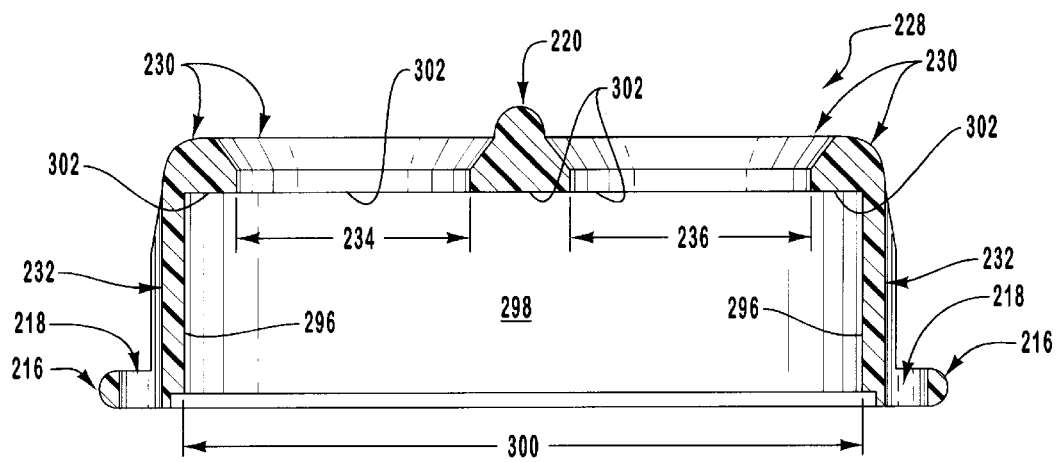
FIG. 22 is a cross-sectional elevation view of the cap of FIG. 19 taken along section line 22—22 shown therein.

Cap 228 is depicted in FIG. 22. There skirt 232 of cap 228 can be seen to have an inner surface 296 that encircles a receiving chamber 298. Receiving chamber 298 opens outwardly at a housing assembly entrance 300 that is encircled by suture ring 216. The end of receiving chamber 298 opposite from housing assembly entrance 300 is, however, only partially closed, being bounded by an inner surface 302 of top wall 230 through which are formed first access aperture 234 and second access aperture 236.

Base 226 is depicted in FIG. 23. There a lip 256 can be seen to project upwardly from top surface 258 of sidewall 242 at the outer edge thereof As a result, lip 256 and sidewall 242 share a common outer surface 304. Cloison 254 projects upwardly from top surface 248 of the central portion of three-layered interior wall 244. The top of each of first fluid reservoir 250 and second fluid reservoir 252 is defined by a plane $P_1$ that contains top surface 258 and top surface 248 of the various walls of base 226. Cloison 254 extends from top surface 248 of interior wall 244 across plane $P_1$. Lip 256 has a continuous encircling top surface 306 that defines a plane $P_2$ that is disposed parallel to plane $P_1$.

Figure 24:
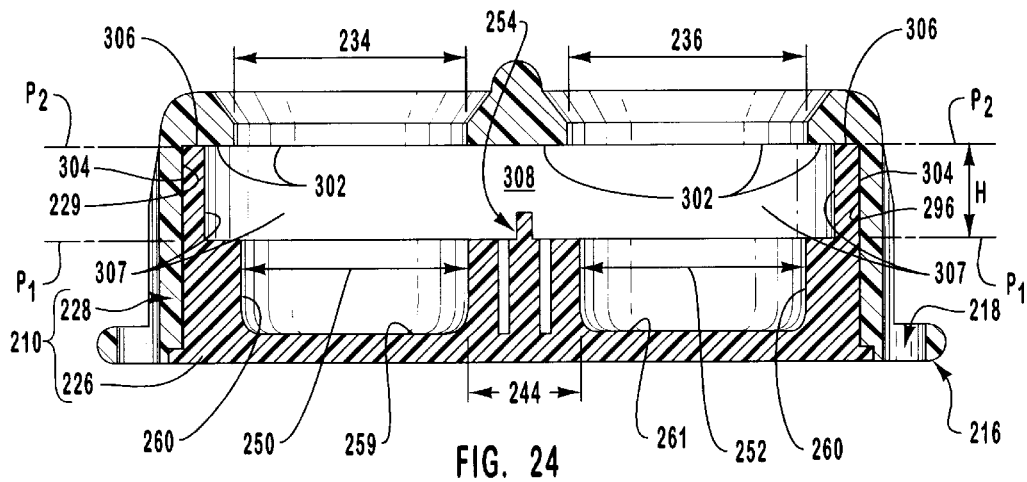
FIG. 24 is a cross-sectional elevation view of the base of FIG. 23 received in the cap of FIG. 22.

FIG. 24 illustrates the relationship among the structures of cap 228 and base 226, when base 226 is received in cap 228. Common outer surface 304 of sidewall 242 and lip 256 of base 226 fits tightly within receiving chamber 298 in cap 228 with top surface 306 of lip 256 in abutment against inner surface 302 of top wall 230 of cap 228. The portion of receiving chamber 298 not filled in this manner by base 226 and not intended to function as part of first fluid reservoir 250 or second fluid reservoir 252 is a void that instead defines a web-receiving chamber 308 between plane $P_1$ and plane $P_2$. The height H of web receiving chamber 308 corresponds to the distance between plane $P_1$ and plane $P_2$.

With base 226 assembled in cap 228, first access aperture 234 and second access aperture 236 communicate between the exterior of housing 210 and one side of web-receiving chamber 308. The opposite side of web-receiving chamber 308 communicates with first fluid reservoir 250 and second fluid reservoir 252.

Returning to FIG. 19, it can be appreciated that in addition to the elements of housing 210 discussed above, vascular access port 202 includes a third element, a needle-penetrable elastomeric compound septum 310 that includes a generally planar oval septum web 312 having a top surface 314 from which first target dome 212 of first septum 206 and second target dome 214 of second septum 208 project. In the assembled state of vascular access port 202, compound septum 310 is disposed against top surface 258 and top surface 248 of side wall 242 and interior wall 244, respectively, of base 226, covering both first fluid reservoir 250 and second fluid reservoir 252. Accordingly, in vascular access port 202, as in vascular access port 70, a single needle-impenetrable elastomeric article is used simultaneously to seal each of the distinct fluid reservoirs therewithin.

While compound septum 310 prevents the transfer of fluids between the exterior of vascular access port 202 and each of first fluid reservoir 250 and second fluid reservoir 252, compound septum 310 also prevents the passage of fluid between first fluid reservoir 250 and second fluid reservoir 252. Like the integrated structure of compound septum 146 of vascular access port 70, compound septum 310 in vascular access port 202 reduces the number of parts required in the assembly of vascular access port 202 and also produces economies of size in housing 210 of vascular access port 202 relative to dual reservoir vascular access ports that employ a pair of individual septums.

Figure 25:
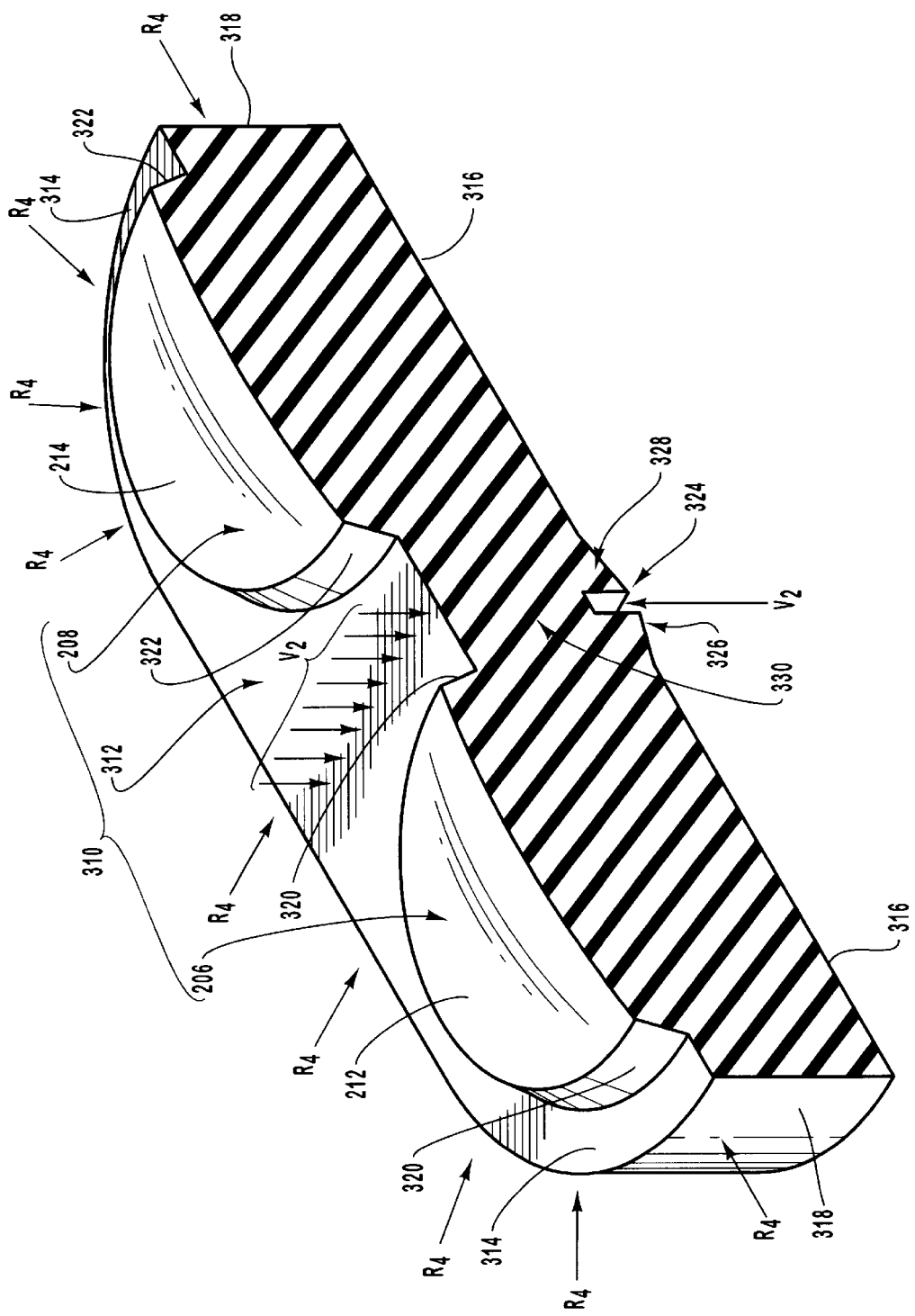
FIG. 25 is a cross-sectional perspective elevation view of the compound septum of FIG. 19 taken along section line 25—25 shown therein.

In view of the significance of compound septum 310, a closer exploration of the structure thereof will be undertaken in relation to FIG. 25. There, septum web 312 of compound septum 310 can be seen to be a planar structure having top surface 314, a lower surface 316 is parallel thereto, and a continuous side surface 318 extending between top surface 314 and lower surface 316. First target dome 212 of first septum 206 has a circular perimeter 320 that is substantially the same size and shape as that of first access aperture 234 in top wall 230 of cap 228. Together first target dome 212 and the portion of septum web 312 located thereunder function as first septum 206. Second target dome 214 of second septum 208 also has a circular perimeter 322 that is substantially similar in size and shape as that of second access aperture 236. Together second target dome 214 and the portion of septum web 312 located thereunder function as second septum 208.

Compound septum 310 is configured to have the same desirable properties in the installed configuration thereof when captured in vascular access port 202 as were discussed above relative to the installed configuration of compound septum 146 in vascular access port 70. By contrast to compound septum 146, however, compound septum 310 includes no septum plugs projecting from lower surface 316 of septum web 312 comparable to first septum plug 182 and second septum plug 184 of compound septum 146.

Therefore, to successfully function in the several intended roles thereof, and to exhibit the desirable properties of sufficient and uniform sealing effectiveness and needle retention force in the installed configuration thereof, various specific design features are incorporated into compound septum 310.

First, compound septum 310 includes an isolation groove 324 recessed in and traversing lower surface 316 of septum web 312 at a location intermediate first target dome 212 and second target dome 214. When housing 210 is assembled capturing compound septum 310 therein, isolation groove 324 receives cloison 254 that is shown, for example in FIGS.

23 and 24, upstanding from interior wall 244 of base 226. The cooperating action of cloison 254 within isolation groove 324 isolates first fluid reservoir 250 from second fluid reservoir 252.

In addition, projecting from lower surface 316 of septum web 312 is a first sealing ridge 326 on one side of isolation groove 324 and a second sealing ridge 328 on the side of isolation groove 324 opposite from first sealing ridge 326. First sealing ridge 326 and second sealing ridge 328 are each proximate to isolation groove 324 oriented parallel thereto. First sealing ridge 326 is thus disposed on lower surface 316 of septum web 312 between isolation groove 324 and first target dome 212. Second sealing ridge 328 is located on lower surface 316 of septum web 312 between isolation groove 324 and second target dome 214.

While first sealing ridge 326 and second sealing ridge 328 assist in some measure in the function of isolating first fluid reservoir 250 from second fluid reservoir 252, an additional function performed by first sealing ridge 326 and second sealing ridge 328 is that of preventing fluid from first fluid reservoir 250 or second fluid reservoir 252, respectively, from entering voids 246 of the type shown in FIGS. 20 and 23 in interior wall 244 of base 226.

In the assembly of housing 210 of vascular access port 202, septum web 312 of compound septum 310 illustrated in FIG. 19, becomes disposed in web-receiving chamber 308 illustrated in FIG. 24. Septum web 312 is correspondingly carefully sized relative thereto. In areas of septum web 312 other than in a central region 330 thereof supporting isolation groove 324, first sealing ridge 326, and second sealing ridge 328, septum web 312 has a thickness as measured between top surface 314 and lower surface 316 thereof that is approximately equal to height H of web-receiving chamber 308 illustrated in FIG. 24. As a result, when compound septum 310 is captured in housing 210, little axially-directed strain of any significance is imposed on septum web 312, other than in central region 330. The axially-directed strain that is imposed on central region 330 and septum web 312 will be explored further relative to FIGS. 27 and 30.

This generalization about the axial-directed strain imposed on central region 330 must be qualified to a degree by a consideration that of necessity arises in connection with the assembly of compound septum web 312 in housing 210. The thickness of septum web 312 preferably exceeds just slightly the height H of web-receiving chamber 308. This insures the development of contact by each point on the outer surfaces of septum web 312 with a corresponding interior surface of housing 210. Thus, each point on top surface 314 of septum web 312 engages some part of inner surface 302 of top wall 230 of cap 228. This occurs at plane $P_2$. Similarly, each point on lower surface 316 of septum web 312 engages one or the other of top surface 258 of sidewall 242 or top surface 248 of interior wall 244 of base 226. This occurs at plane $P_1$.

Septum web 312 has an outer perimeter defined by side surface 318 thereof Inner surface 307 of lip 256 of base 226 correspondingly defines the perimeter of web-receiving chamber 308. The exterior perimeter of septum web 312 is, however, larger in cross-sectional area and in most other specific dimensions in the plane of septum web 312 than is inner surface 307 of lip 256 of housing 210. The difference in perimeter sizes is sufficiently small to allow septum web 312 to be disposed manually in lip 256 without causing buckling in compound septum 310. As a result, inner surface 307 of lip 256 of base 226 imposes radially inwardly directed forces designated by arrows $R_4$ in FIG. 25 to side surface 318 of septum web 312. The forces $R_4$ in turn radially inwardly displace side surface 318 of septum web 312 to a relatively uniform extent.

Accordingly, it is one aspect of the present invention that a compound septum, such as compound septum 310 illustrated in FIG. 25, includes reservoir segregation means on the lower side of the septum web thereof for performing the function of isolating the distinct fluid reservoirs in the dual reservoir vascular access port with which the compound septum is utilized. By way of example and not limitation, structures disclosed herein capable of performing the function of such a reservoir segregation means include isolation groove 324 that is recessed in and traverses lower surface 316 of septum web 312. It is the cooperative action produced by isolation groove 324 in cloison 254 on base 226 that enables this essential function to occur.

Alternatively, other configurations of structures formed on lower surface 316 of septum web 312 could have a similarly efficacious result, when utilized with correspondingly configured matingly cooperating structures on base 226. For example, isolation groove 324 need not be linear or even continuous in order to effectively isolate first fluid reservoir 250 from second fluid reservoir 252, if appropriate cooperating structures are provided on base 226. A raised structure on lower surface 316 of septum web 312 could with a satisfactory degree of effectiveness cooperate with a recessed structure in base 226 to perform the function of isolating first fluid reservoir 250 from second fluid reservoir 252.

The effectiveness of isolation groove 324 is enhanced to a degree by the application to central region 330 of septum web 312 immediately about isolation groove 324 of axially directed compressive strain, when compound septum 310 is captured in housing 310.

A reservoir segregation means according to the teachings of the present invention could include first sealing ridge 326 and second sealing ridge 328, alternatively to or in addition to isolation groove 324. Neither of first sealing ridge 326 or second sealing ridge 328 need necessarily be linear as disclosed herein or disposed in a parallel relationship to isolation groove 324 or any structure equivalent thereto utilized to perform the function of the reservoir segregation means.

Figure 26:
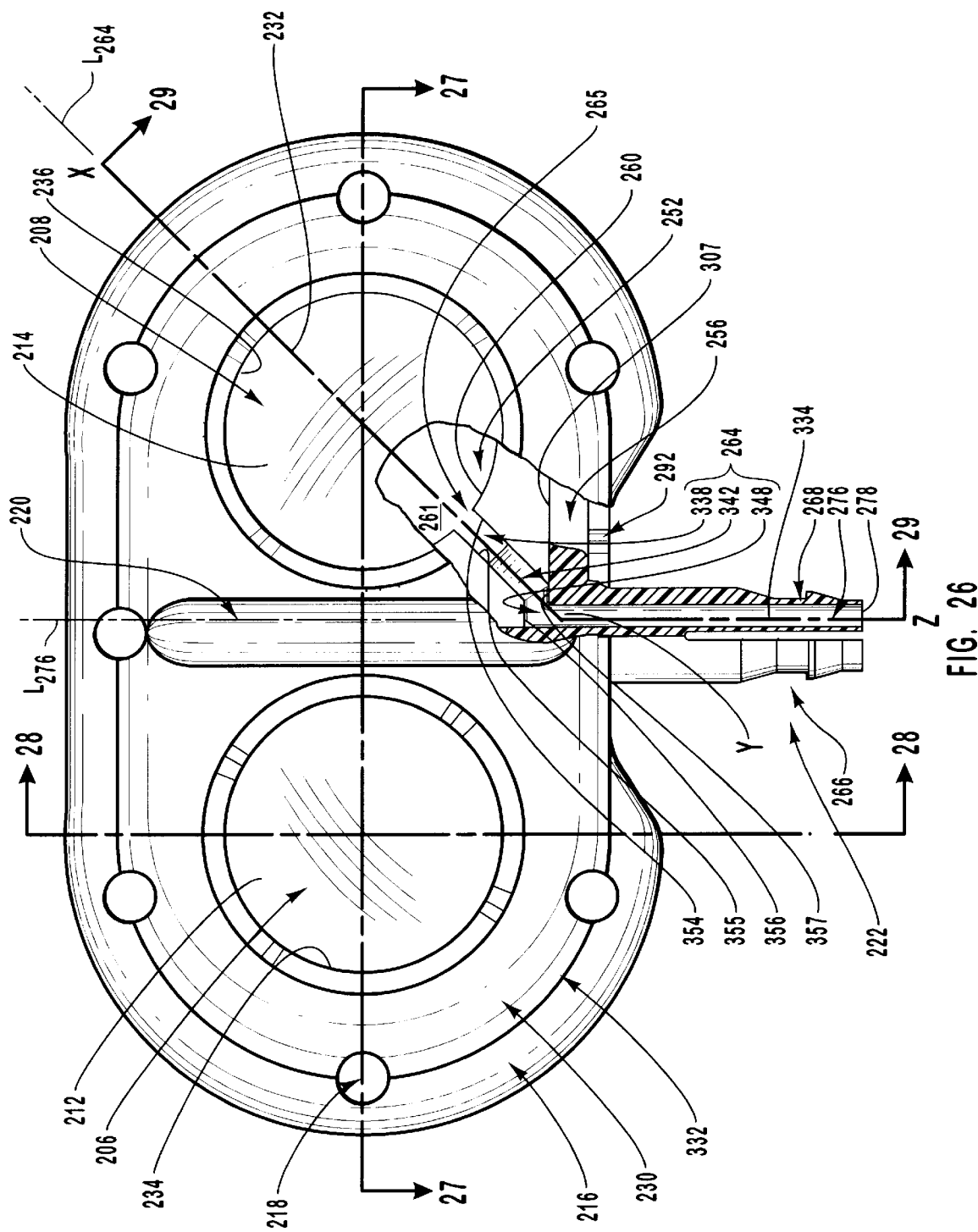
FIG. 26 is a plan view of the assembled vascular access port of FIG. 18.

FIG. 26 is an enlarged plan view of the assembled vascular access port 202 shown in FIG. 18. To facilitate an enhanced understanding of the interaction of the components of vascular access port 202 in the immediate vicinity of first fluid channel 262 and second fluid channel 264, the portion of the assembled vascular access port 202 overlying the open top of second fluid channel 264 in base 226 and enclosed second fluid passageway 276 in second prong 268 of outlet stem 222 has been broken away. As a result, the elements of second fluid channel 264 can be explored in additional detail. Naturally, second fluid channel 264 is typical, if not identical, in structure to first fluid channel 262, which has not been rendered visible in FIG. 26 by breaking away corresponding overlying portions of vascular access port 202. In addition, FIG. 26 also serves to carefully define a number of subsequently presented cross-sectional elevation views of vascular access port 202 in an assembled condition thereof The first of these cross-sectional views is the elevation view of vascular access port 202 shown in FIG. 27. There the elements of compound septum 310 are shown captured in housing 210 of vascular access port 202. Septum web 312 of compound septum 310 has been reduced in thickness to height H of web-receiving chamber 308 that is filled by septum web 312 and, that is therefore, not shown in FIG. 27.

Figure 27:
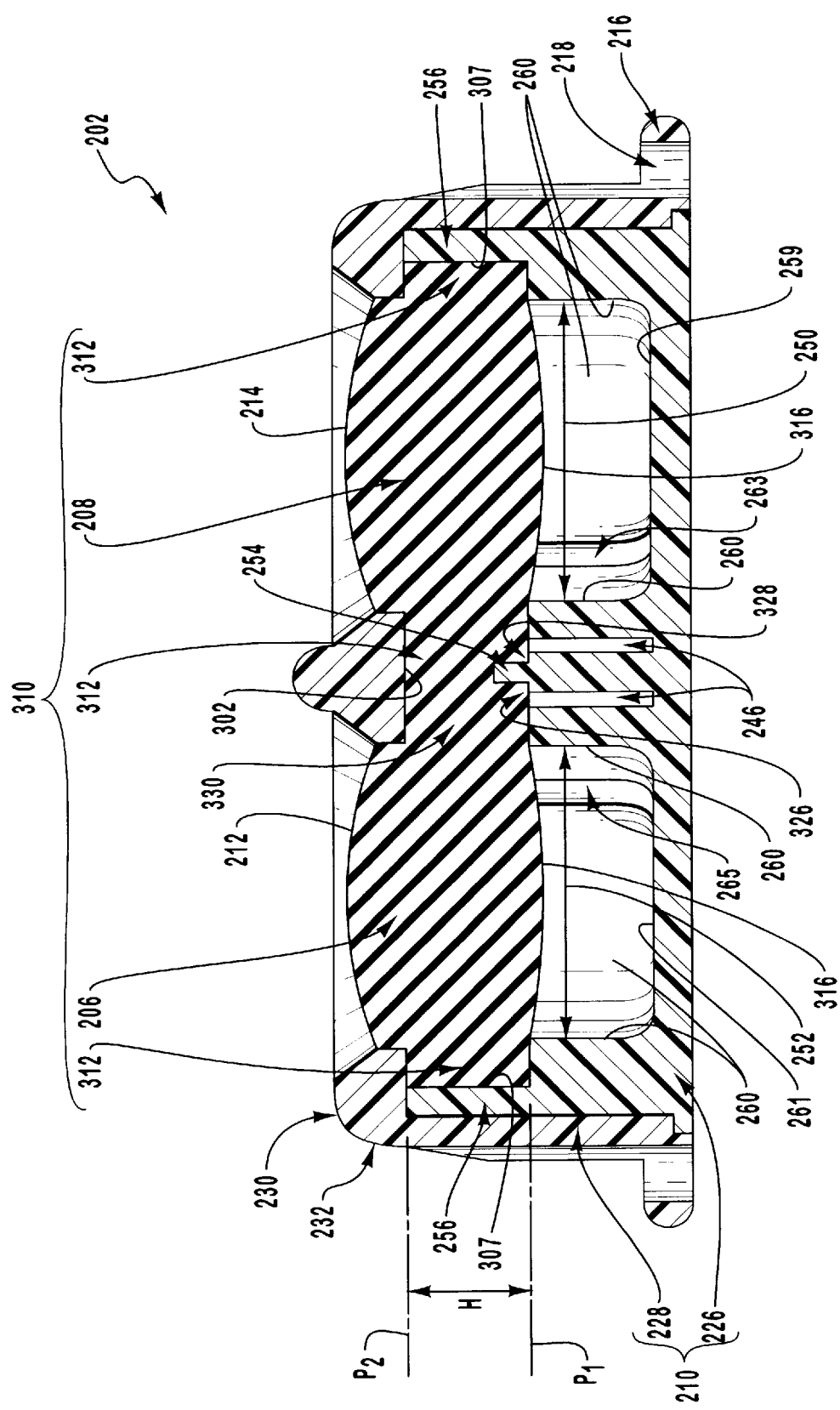
FIG. 27 is a cross-sectional elevation view of the assembled vascular access port of FIG. 26 taken along section line 27—27 shown therein.

In central region 330 of septum web 312, first sealing ridge 326 and second sealing ridge 328 have been forced into alignment with plane $P_1$, thereby assisting cloison 254 in isolating first fluid reservoir 250 from second fluid reservoir 252. First sealing ridge 326 and second sealing ridge 328 also prevent the entrance of fluid from either of first fluid reservoir 250 or second fluid reservoir 252 into voids 246 shown. The inward displacement of the outer periphery of septum web 312 by inner surface 307 of lip 256 of base 226 in combination with the axial displacement of septum web 312 in central region 330 thereof causes lower surface 316 of septum web 312 to bulge outwardly and downwardly into first fluid reservoir 250 and into second fluid reservoir 252 as seen in FIG. 27. The change in shape of the profile of compound septum 310 in the installed configuration thereof relative to the profile of compound septum 310 in the natural configuration thereof shown in FIG. 25 will be explored in additional detail relative to FIG. 30.

Finally, FIG. 27 includes an elevation view of first slot 263 that is the proximal entrance to first open-topped fluid channel 262 from first fluid reservoir 250. Also shown is second slot 265 that is the proximal entrance to open-topped second fluid channel 264 from second fluid reservoir 252. Neither first fluid channel 262, nor second fluid channel 264 are, however, shown in FIG. 27. Each appear clearly in the plan view presented in FIG. 21.

Figure 28:
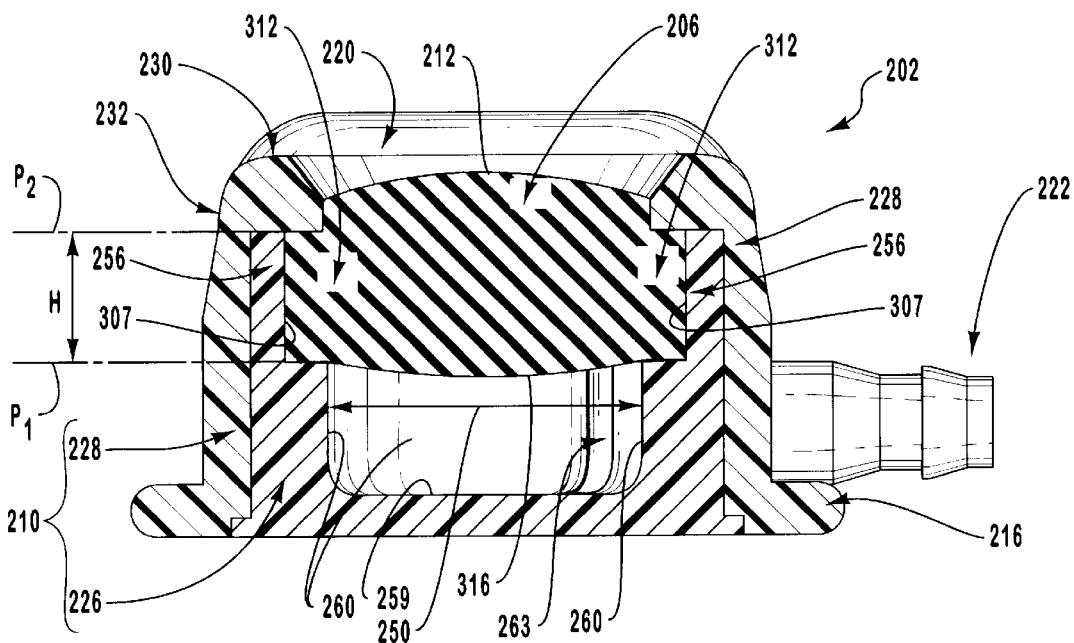
FIG. 28 is a cross-sectional elevation side view of the assembled vascular access port of FIG. 26 taken along section line 28—28 shown therein.

The second cross-sectional presentation of vascular access port 202 is shown in FIG. 28. There also septum web 312 of compound septum 310 is shown with the periphery thereof inwardly displaced by inner surface 307 of lip 256 of base 226. Correspondingly, lower surface 316 of septum web 312 bulges slightly outwardly and downwardly into first fluid reservoir 250 as seen in FIG. 28. First slot 263 in inner surface 260 of the remainder of first fluid reservoir 250 is also shown. First slot 263 leads by way of open-topped first fluid channel 262 shown in FIG. 21 to first fluid passageway 272 in outlet stem 222, although neither first fluid passageway 272 nor open-topped first fluid channel 262 is shown in FIG. 28.

Figure 29:
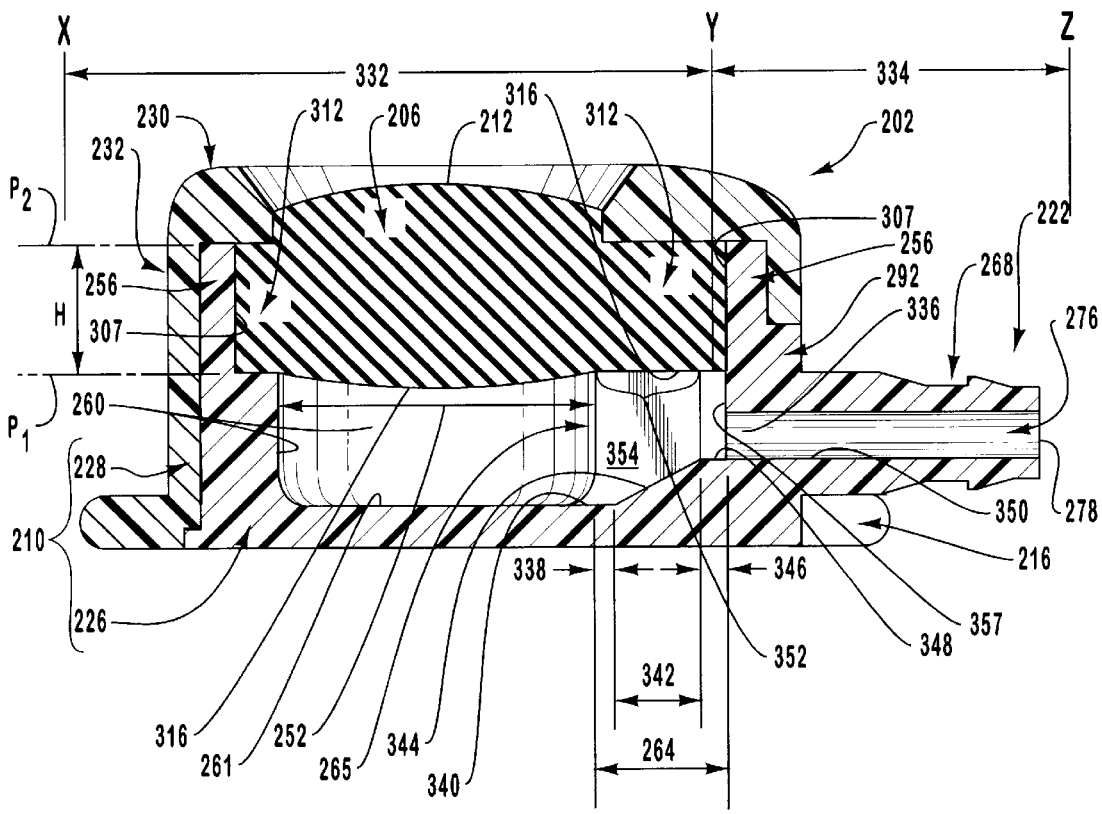
FIG. 29 is a cross-sectional elevation view of the assembled vascular access port of FIG. 26 taken along the non-planar section line 29—29 shown therein.

Finally, a non-planar cross-sectional elevation view taken along section line 29—29 in FIG. 26 is presented in FIG. 29. The orientation of each leg of section line 29—29 has been carefully selected to coincide with the various passageways by which fluid flow to or from second fluid reservoir 252 is effected through outlet stem 222.

A first leg 332 of section line 29—29 extends from a point X at the upper right hand end of section line 29—29 to a point Y at which section line 29—29 in FIG. 26 is seen to bend. First leg 332 of section line 29—29 traverses second fluid reservoir 252 at such an angle as to coincide with the center of second fluid channel 264 and extend along longitudinal axis $L_{264}$ thereof originally introduced relative to FIG. 21. A second leg 334 of section line 29—29 extends from the bend at point Y in section line 29—29 to a point Z at the bottom of FIG. 26. Accordingly, second leg 334 of section line 29—29 coincides with longitudinal axis $L_{276}$ of enclosed second fluid passageway 276 in second prong 268 of outlet stem 222 that was originally also introduced relative to FIG. 21. The position of each of point X, point Y, and point Z is correspondingly identified in the cross-sectional elevation view of FIG. 29.

Of particular interest in FIG. 29 are the various regions of open-topped second fluid channel 264, as well as the interaction of septum web 312 of compound septum 310 with the open top of second fluid channel 264. The regions and interactions relative to second fluid channel 264 are typical of those existing relative to first fluid channel 262.

In FIG. 29, second slot 265 in inner surface 260 of second fluid reservoir 252 appears on edge. Second slot 265 does, however, demarcate the proximal terminus of second fluid channel 264. The opposite or distal terminus of second fluid channel 264 is at the proximal end 336 of second fluid passageway 276 formed in second prong 268 of outlet stem 222. Between these two extremes, second fluid passageway 276 includes three distinct regions.

Moving from the proximal boundary of second fluid channel 264 at second slot 265, second fluid channel 264 first includes an inner region 338, the floor 340 of which is coplanar with inner floor 261 of second fluid reservoir 252. Continuing along second fluid channel 264 from inner region 338 thereof, second fluid channel 264 includes a relatively lengthy medial region 342, the interior wall 344 of which slopes upwardly from floor 340 of inner region 338. The slope of floor 344 of medial region 342 of second fluid channel 264 continues distally along second fluid channel 264 to an outer region 346 thereof that communicates directly with proximal end 336 of second fluid passageway 276. Outer region 346 of second fluid channel 264 has a horizontal floor 348 that is coincident with the lower floor 350 of second fluid passageway 276 in second prong 268 of outlet stem 222.

Inner region 338 has walls 354, 355 that both appear only in FIG. 26. Walls 354, 355 of inner region 338 are disposed normal to inner floor 261 of second fluid reservoir 252 and are also parallel to each other. Medial region 342 shares walls 354, 355 with inner region 338. Outer region 346 has walls 356, 357 that both appear only in FIG. 26. Walls 356, 357 of outer region 346 of second fluid channel 264 are oriented at a common obtuse angle to walls 354, 355, respectively, and are parallel to each other. Wall 357 is coplanar with inner surface 307 of lip 256 of base 226 on the side thereof from which outlet stem 222 projects.

In the manufacture of base 226 of housing 210 of vascular access port 202, each of the closed fluid passageways in outlet stem 222, such as second fluid passageway 276, is maintained during injection molding by the insertion of a removable mandrel pin having a cross section corresponding to that intended in each respective fluid flow passageway. The balance of the structure of base 226, including the entire length of second fluid channel 264, is entirely free of undercuts that might further complicate the injection molding process.

As in FIGS. 27 and 28, a portion of lower surface 316 of septum web 312 of compound septum 310 bulges downwardly as shown in FIG. 29 into second fluid flow reservoir 252. Nonetheless, the open top of second fluid channel 264 is also sealed by a relatively lengthy portion of lower surface 316 of septum web 312 that is identified in FIG. 29 as channel sealing portion 352. Therefore, it is not only the top of each of first fluid reservoir 250 and second fluid reservoir 252 that is sealed by compound septum 310, but also the open top of each of first fluid channel 262 and second fluid channel 264.

Figure 30:
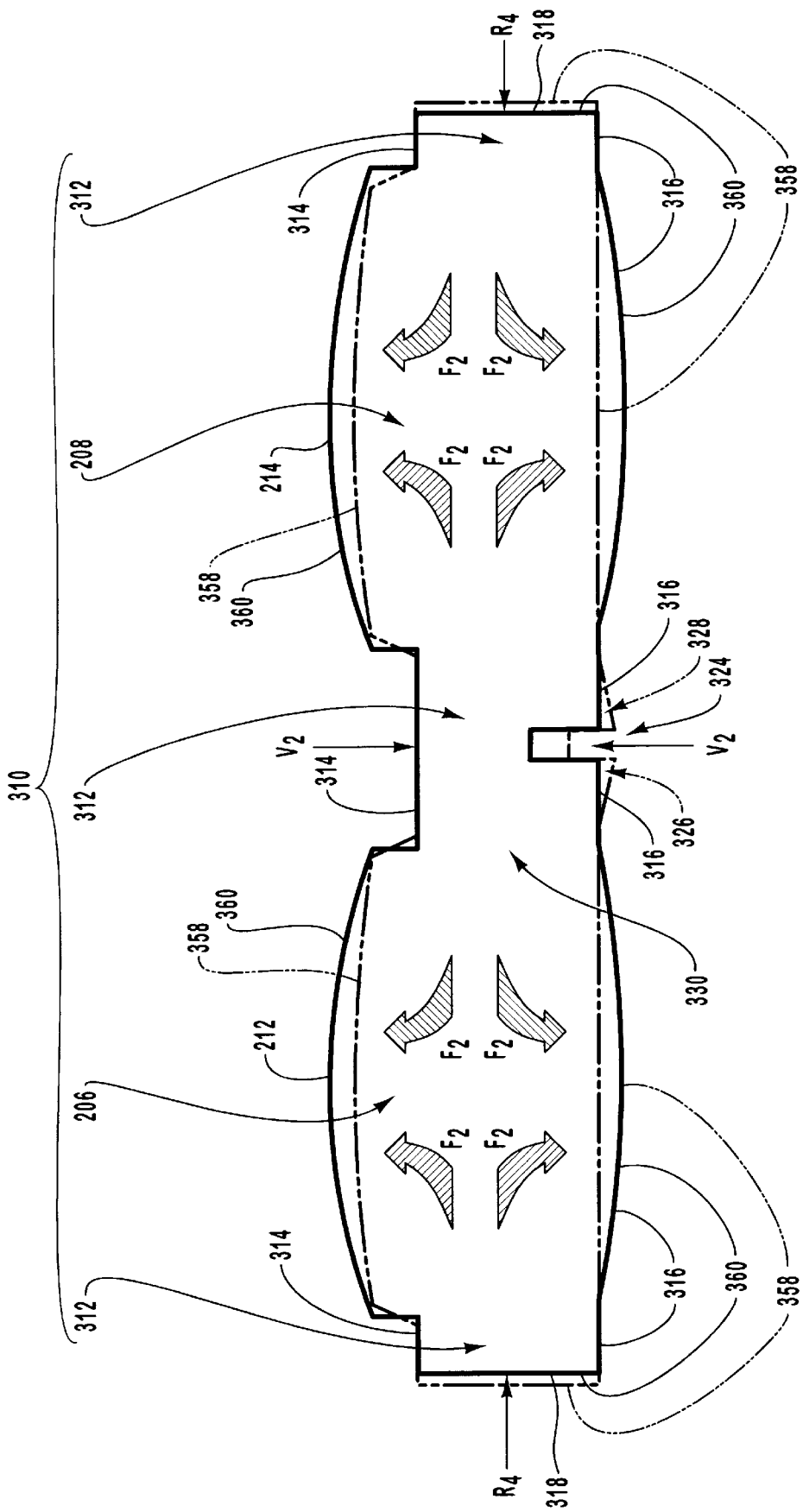
FIG. 30 is a diagram containing superimposed comparative elevation profile views of the compound septum of FIG. 25 in the natural configuration thereof shown in phantom and in the installed configuration thereof as in FIG. 27 shown in solid line.

In FIG. 30, a natural configuration profile 358 of compound septum 310 free from any external forces is shown in phantom. This profile corresponds to the profile appearing in FIG. 25. By way of contrast, however, a superimposed installed configuration profile 360 of compound septum 310 that results from the capture of compound septum 310 in housing 210 of vascular access port 202 is shown in solid line. This profile corresponds to the profile appearing in FIG. 27.

When compound septum 310 is captured in housing 210, two distinct types of forces are applied thereto by interior surfaces of web-receiving chamber 308. First, inner surface 307 of encircling lip 256 on base 226 applies radially inwardly directed relatively uniform forces $R_4$ to side surface 318 of septum web 312. As a result, side surfaces 318 are displaced radially inwardly. Secondly, first sealing ridge 326 and second sealing ridge 328 are displaced upwardly as viewed in FIG. 30 by top surface 248 of interior wall 244 of base 226, and central region 330 of septum web 312 is urged against inner surface 302 of top wall 230 of cap 228 between first access aperture 234 and second access aperture 236. This produces axially-directed forces $V_2$ on central region 330 of septum web 312. At locations other than central region 330, septum web 312 is not intended to be exposed to significant axially-directed forces, such as axially-directed forces $V_2$.

Nonetheless, radially directed forces $R_4$ and axially-directed forces $V_2$ shown in FIG. 30 do result in the development of strains and changes in hydrostatic pressure within the material of compound septum 310. A portion of the material of compound septum 310 is induced thereby to flow radially inwardly into first septum 206 and second septum 208 as represented by arrows $F_2$. The material displacement increases the thickness of first septum 206 and second septum 208, causing lower surface 316 of septum web 312 to bulge downwardly into a corresponding fluid reservoir of vascular access port 202. Simultaneously, first target dome 212 and second target dome 214 are lifted upwardly through first access aperture 234 and second access aperture 236, respectively, toward the exterior of vascular access port 202.

This combination of forces applied to compound septum 310 results in the sealing of first access aperture 234 and second access aperture 236, the isolation of first fluid reservoir 250 from second fluid reservoir 252, and the development of uniform hydrostatic pressure in the portions of compound septum 310, namely first septum 206 and second septum 208, likely to be penetrated by the tip of a hypodermic needle. This in turn produces uniform sealing and needle retention properties in those portions of compound septum 310.

Figure 31:
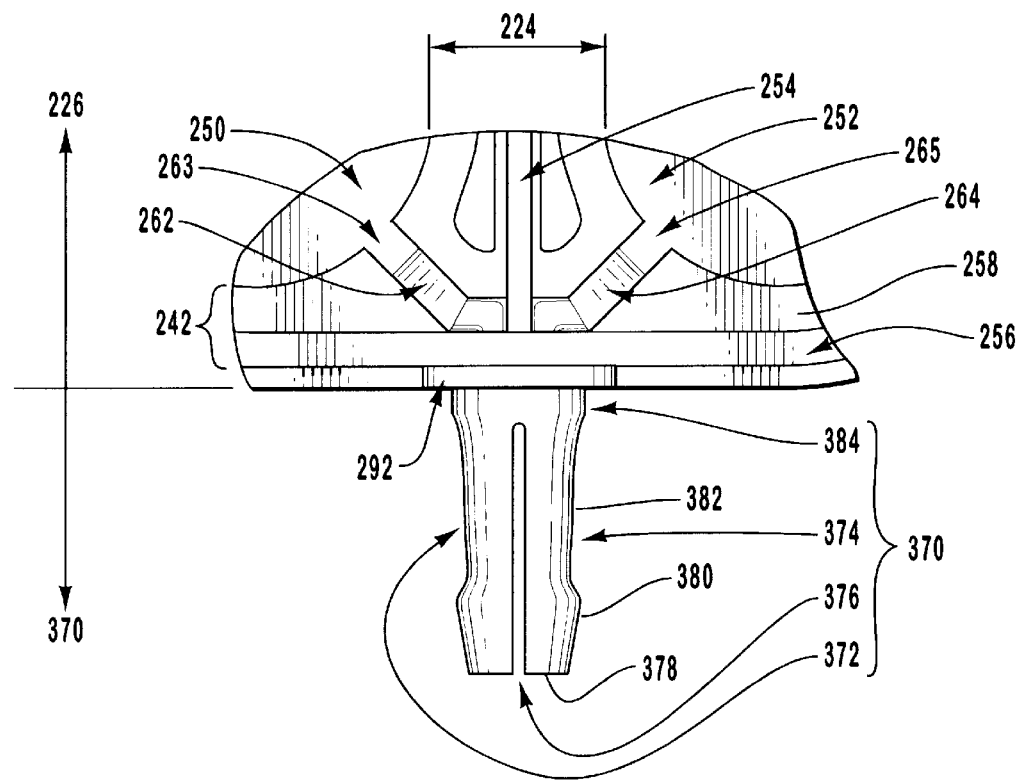
FIG. 31 is a plan view of an alternative embodiment of the outlet stem of FIGS. 20 and 21.

An alternative embodiment of an outlet stem for use with a vascular access port incorporating teachings in the present invention is shown in FIG. 31. There, an outlet stem 370 integrally formed with base 226 of vascular access port 202 is shown as including a first prong 372 and a second prong 374 disposed parallel to and separated from first prong 372. The exterior of each of first prong 372 and second prong 374 is identical. Only those structures on the exterior of second prong 374 will accordingly be discussed, although it is appropriate to note that an outlet stem, such as outlet stem 370, is most optimally adapted for use with a 10 French dual lumen vascular access catheter made of soft medical grade silicone.

Progressing from free distal end 378 of second prong 374, the exterior of second prong 374 includes first a relatively round-shouldered barb 380, and thereafter a semi-cylindrical main portion 382. Between the closed end of elongated slot 376 and the exterior of sidewall 242 of base 226, first prong 372 and second prong 374 merge into a single unified cylindrical base 384 for outlet stem 370. Cylindrical base 384 of outlet stem 370 is joined with base 226 of housing 210 at shoulder 292 on the exterior of sidewall 242.

Figure 32:
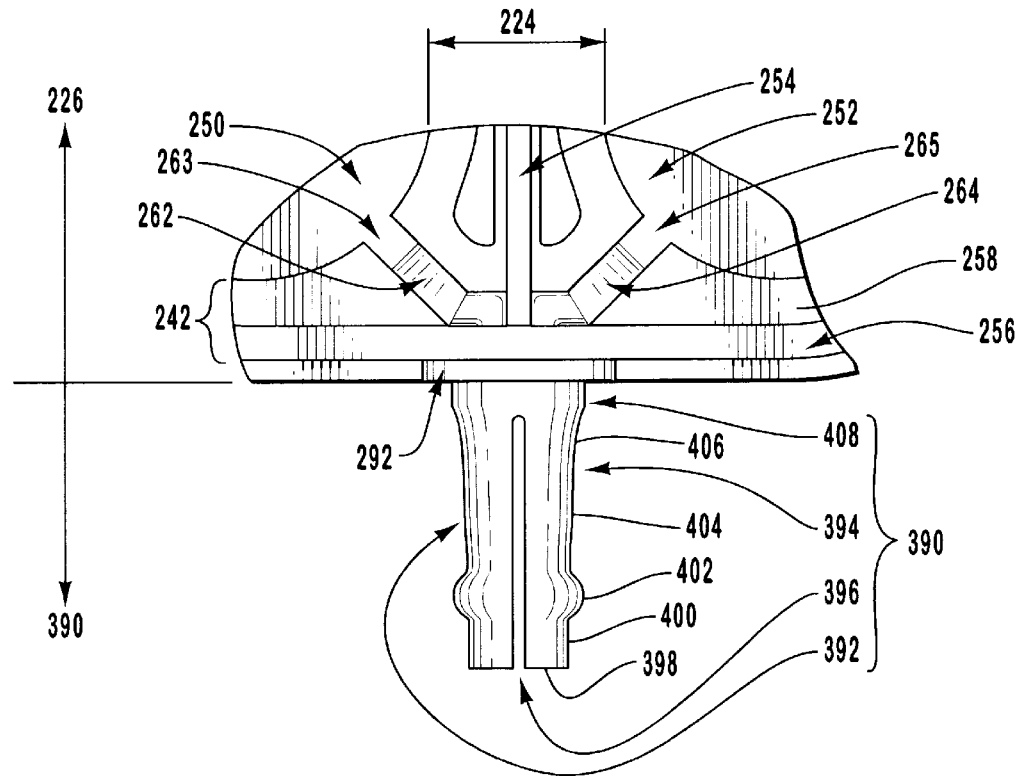
FIG. 32 is a plan view of another alternative embodiment of the outlet stem of FIGS. 20 and 21.

Yet another embodiment of an outlet stem for use with a vascular access port incorporating teachings of the present invention is shown in FIG. 32. There, an outlet stem 390 integrally formed with base 226 of vascular access port 202 is shown as including a first prong 392 and a second prong 394 disposed parallel to and separated from first prong 392 by an elongated slot 396. The exterior of each of first prong 392 and second prong 394 is identical. Only those structures on the exterior of second prong 394 will, accordingly, be discussed, although it should be noted that an outlet stem, such as outlet stem 390, is most optimally adapted for use with a dual lumen vascular access catheter made of flexible medical grade silicone in the range of sizes from 9.5 to 10 French.

Progressing from free distal end 398 of second prong 394, the exterior of second prong 394 includes first a semi-cylindrical distal end portion 400, then a bulbous enlargement 402, thereafter a cylindrical medial portion 404, and finally a tapered enlarging portion 406. Between the closed end of elongated slot 396 and the exterior of sidewall 242 of base 226, tapered enlarging portions 406 of first prong 392 and second prong 394 merge into a single unified cylindrical base 408 for outlet stem 390. Cylindrical base 408 of outlet stem 390 is joined with base 226 of housing 210 at shoulder 292 on the exterior of sidewall 242.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A vascular access port having a plurality of distinct fluid reservoirs, said access port comprising:
   a. a needle-impenetrable base, said base comprising:
      i. a bottom wall;
      ii. an encircling sidewall upstanding from said bottom wall; and
      iii. an interior wall upstanding from said bottom wall and interconnecting a pair of nonadjacent locations on the interior of said encircling sidewall, thereby defining interior of said encircling sidewall a first fluid reservoir having a first inner floor and a second fluid reservoir on opposite sides of said interior wall having a second inner floor;
   b. a needle-impenetrable cap configured to receive said base therein, said cap comprising:
      i. a top wall;
      ii. an encircling skirt depending from said top wall;
      iii. a first access aperture formed through said top wall at a position that communicates with said first fluid reservoir, when said base is received in said cap; and
      iv. a second access aperture formed through said top wall at a position that communicates with said second fluid reservoir, when said base is received in said cap; and
   c. a needle-penetrable elastomeric compound septum comprising:
      i. a first target dome disposed in said first access aperture sealing said first access aperture, when said base is received in said cap with said compound septum disposed therebetween;
      ii. a second target dome disposed in said second access aperture sealing said second access aperture, when said base is received in said cap with said compound septum disposed therebetween; and iii. a septum web integrally formed with and interconnecting said first target dome and said second target dome, the side of said septum web opposite from said first target dome and said second target dome defining a lower side of said septum web, said septum web being so configured as to effect fluid isolation of said first fluid reservoir from said second fluid reservoir, when said base is received in said cap with said compound septum disposed therebetween.

2. A vascular access port as recited in claim 1, wherein said septum further comprises a sealing ridge depending from and traversing said lower side of said septum web.

3. An access port as recited in claim 1, wherein:
a. said base further comprises a cloison upstanding from the top of said interior wall interconnecting said pair of nonadjacent locations on said interior of said encircling sidewall; and
b. said compound septum further comprises an isolation groove recessed into and traversing said lower side of said septum web, said cloison being received in said isolation groove when said base is received in said cap with said compound septum disposed therebetween.

4. An access port as recited in claim 3, wherein said compound septum further comprises a pair of sealing ridges depending from said lower side of said septum web adjacent to and on opposite sides of said isolation groove.

5. An access port as recited in claim 3, wherein axially-directed strain is imposed in said septum web between said first target dome and said second target dome by said top of said interior wall of said base and the interior surface of said top wall of said cap intermediate said first access aperture and said second access aperture, when said base is received in said cap with said compound septum disposed therebetween.

6. An access port as recited in claim 1, wherein a web receiving recess is produced between the interior surface of said top wall of said cap and the tops of said sidewall and said interior wall of said base when said base is received in said cap, said web receiving recess having a height approximately equal to the thickness of said septum web.

7. A vascular access port as recited in claim 6, wherein the area of the cross section of said web receiving recess in the plane thereof is less than the area of the cross section of said septum web in said plane thereof.

8. An access port as recited in claim 6, wherein:
a. the maximum extent of said web receiving recess in the plane thereof is less than the maximum extent of said septum web measured in the plane thereof; and
b. the width of said web receiving recess measured in the plane thereof normal to said maximum extent thereof is less than the width of said septum web measured in the plane thereof normal to said maximum extent thereof.

9. An access aperture as recited in claim 1, wherein the thickness of said septum web is less than the thicknesses of each of said first target dome and said second target dome.

10. A vascular access port as recited in claim 1, wherein said compound septum further comprises:
a. an isolation groove recessed into and traversing said lower surface of said septum web intermediate said first target dome and second target dome;
b. a first sealing ridge depending from said lower surface of said septum web on a first side of said isolation groove; and
c. a second sealing ridge depending from said lower surface of said septum web on a second side of said isolation groove opposite from said first side thereof.

11. A vascular access port having a plurality of distinct fluid reservoirs, said access port comprising:
a. a needle-impenetrable housing enclosing a first fluid reservoir and a second fluid reservoir, said housing defining a first access aperture communicating through said housing with said first fluid reservoir and a second access aperture communicating through said housing with said second fluid reservoir, said housing comprising:
i. a needle-impenetrable base having a flat inner floor and walls normal thereto and upstanding therefrom, said walls defining said first fluid reservoir and said second fluid reservoir;
ii. an outlet stem integrally formed with said base projecting from the exterior of one of said walls thereof and enclosing in side-by-side relationship extending longitudinally therethrough a first fluid passageway and a second fluid passageway;
iii. an open-topped first fluid channel communicating between said first fluid reservoir and said first fluid passageway in said outlet stem;
iv. an open-topped second fluid channel communicating between said second fluid reservoir and said second fluid passageway in said outlet stem; and
v. a needle-impenetrable cap configured to receive said base, said cap comprising a top wall having formed therethrough said first access aperture and said second access aperture;
b. a needle-penetrable elastomeric first septum captured by said housing and sealing said first access aperture, said first septum comprising:
i. a first target dome positioned in said first access aperture, when said base is received in said cap with said first septum disposed therebetween; and
ii. a first septum web integrally formed with and encircling said first target dome, a portion of said first septum web closing the open top of said first fluid channel, when said base is received in said cap with said first septum disposed therebetween; and
c. a needle-penetrable elastomeric second septum captured by said housing and sealing said second access aperture, said second septum comprising:
i. a second target dome positioned in said second access aperture, when said base is received in said cap with said second septum disposed therebetween; and
ii. a second septum web integrally formed with and encircling said second target dome, a portion of said second septum web closing the open top of said second fluid channel, when said base is received in said cap with said second septum disposed therebetween.

12. An access port as recited in claim 11, wherein:
a. the thickness of said first septum web is less than the thickness of said first target dome; and
b. the thickness of said second septum web is less than the thickness of said second target dome.

13. An access port as recited in claim 11, wherein;
a. said first septum web is generally planar, and
b. said second web is generally planar.

14. An access port as recited in claim 13, wherein said first septum web is generally coplanar with said second septum web, when said first septum and said second septum are captured by said housing.

15. An access port as recited in claim 13, wherein said first septum web is integrally interconnected with said second septum web.

16. An access port as recited in claim 13, wherein;
   a. the cross section of said first target dome in a plane parallel to said first septum web is substantially congruent to the cross section of said first access aperture; and
   b. the cross section of said second target dome in a plane parallel to said second septum web is substantially congruent to the cross section of said second access aperture.

17. An access port as recited in claim 16, wherein:
   a. said cross section of said first target dome is circular; and
   b. said cross section of said second target dome is circular.

18. An access port as recited in claim 13, wherein:
   a. when said first septum and said second septum are captured by said housing, the side of said first septum web opposite from said first target dome and the side of said second septum web opposite from said second target dome define a common plane; and
   b. said base further comprises a cloison upstanding from the top of one of said walls of said base located between said first fluid cavity and said second fluid cavity, said cloison projecting toward and across said common plane.

19. An access port as recited in claim 11, wherein:
   a. said first fluid channel is substantially linear, and the longitudinal axis of said first fluid channel is disposed at an angle of about 45° to the longitudinal axis of said first fluid passageway proximal of said outlet stem; and
   b. said second fluid channel is substantially linear, and the longitudinal axis of said second fluid channel is disposed at an angle of about 45° to the longitudinal axis of said second fluid passageway proximal of said outlet stem.

20. A vascular access port as recited in claim 11, wherein:
   a. said first fluid channel has sides that are perpendicular to said inner floor of said base; and
   b. said second fluid channel has sides that are perpendicular to said inner floor of said base.

21. A compound septum for use in an implantable dual reservoir vascular access port of the type having a needle-impenetrable housing enclosing distinct first and second fluid reservoirs accessible from the exterior of the access port through corresponding first and second access apertures formed through a wall of the housing, said compound septum comprising:
   a. a needle-penetrable elastomeric first target dome exposable to the exterior of the housing through the first access aperture;
   b. a needle-penetrable elastomeric second target dome exposable to the exterior of the housing through the second access aperture;
   c. an elastomeric septum web integrally formed with and interconnecting said first target dome and said second target dome, the side of said septum web opposite from said first target dome and said second target dome defining a lower side of said septum web, said septum web being enclosed in the housing when said first target dome and said second target dome are exposed to the exterior of the housing through the first access aperture and the second access aperture, respectively; and
   d. reservoir segregation means located between said first target dome and said second target dome on said lower side of said septum web for isolating the first fluid reservoir from the second fluid reservoir.

22. A compound septum as recited in claim 21, wherein said reservoir segregation means comprises an isolation groove recessed into and traversing said lower side of said septum web.

23. A compound septum as recited in claim 22, wherein said reservoir segregation means further comprises:
   a. a first sealing ridge depending from said lower side of said septum web between said isolation groove and said first target dome; and
   b. a second sealing ridge depending from said lower side of said septum web between said isolation groove and said second target dome.

24. A compound septum as recited in claim 21, wherein the thickness of said septum web is less than the thickness of each of said first target dome and second target dome.

25. A compound septum as recited in claim 21, wherein said septum web is generally planar.

26. A compound septum as recited in claim 21, wherein:
   a. the shape of the cross section of said first target dome taken in a plane parallel to said septum web is substantially congruent to the shape of the cross section of the first access aperture; and
   b. the shape of the cross section of said second target dome taken in a plane parallel to said septum web is substantially congruent to the shape of the cross section of the second access aperture.

27. A compound septum as recited in claim 26, wherein:
   a. said shape of said cross section of said first target dome circular,
   b. said shape of said cross section of said second target dome is circular; and
   c. the shape of the cross section of said septum web in the plane thereof is oval.

28. A compound septum as recited in claim 21, wherein said septum web encircles said first target dome and said second target dome.

29. A compound septum for use in a implantable dual reservoir vascular access port of the type having a needle-impenetrable housing enclosing distinct first and second fluid reservoirs accessible from the exterior of the access port through corresponding first and second access apertures formed through a wall of the housing, said compound septum comprising:
   a. a needle-penetrable elastomeric first target dome exposable to the exterior of the housing through the first access aperture;
   b. a needle-penetrable elastomeric second target dome exposable to the exterior of the housing through the second access aperture; and
   c. an elastomeric septum web integrally formed with and interconnecting said first target dome and said second target dome, the side of said septum web opposite from said first target dome and said second target dome defining a lower surface of said septum web, said septum web being enclosed in the housing when said first target dome and said second target dome are exposed to the exterior of the housing through the first access aperture and the second access aperture, respectively;
   d. an isolation groove recessed into and traversing said lower surface of said septum web intermediate said first target dome and said second target dome;
   e. a first sealing ridge depending from said lower surface of said septum web proximate and parallel to said isolation groove; and f. a second sealing ridge depending from said lower surface of said septum web proximate and parallel to said isolation groove on the side of said isolation groove opposite from said first sealing ridge.

30. A base for a needle-impenetrable housing of a vascular access port of the type having a first fluid reservoir with a first inner floor and a second fluid reservoir with a second inner floor, the first and second fluid reservoirs being accessible from the exterior of the housing through respective first and second access apertures formed through a cap of the housing that receives the base of the housing in the assembled condition of the housing, said base comprising:

a. a bottom wall;

b. an encircling sidewall upstanding from said bottom wall;

c. an interior wall upstanding from said bottom wall interconnecting a pair of non-adjacent locations on the interior of said encircling sidewall, thereby defining interior of said encircling sidewall on opposite sides of said interior wall the first fluid reservoir and the second fluid reservoir of the vascular access port;

d. an outlet stem integrally formed with and projecting from the exterior of said encircling sidewall of said base, said outlet stem enclosing in side-by-side relationship extending longitudinally therethrough a first fluid passageway and a second fluid passageway;

e. an open-topped first fluid channel communicating between the first fluid reservoir of the access port and said first fluid passageway in said outlet stem; and f. an open-topped second fluid channel communicating between the second fluid reservoir of the access port and said second fluid passageway in said outlet stem.

31. A base for a housing as recited in claim 30, wherein said first fluid channel communicates with said first fluid passageway at the proximal end of said first fluid passageway.

32. A base for a housing as recited in claim 30, wherein:

a. said first fluid channel is substantially linear, and the longitudinal axis of said first fluid channel is disposed at a first acute angle to the longitudinal axis of said first fluid passageway proximal of said outlet stems; and b. said second fluid channel is substantially linear, and the longitudinal axis of said first fluid channel is disposed at a second acute angle to the longitudinal axis of said second fluid passageway proximal of said outlet stem.

33. A base for a housing as recited in claim 32, wherein said first acute angel is equal to about 45°.

34. A base for a housing as recited in claim 32, wherein said second acute angel is equal to about 45°.

35. A base for a housing as recited in claim 30, wherein said first fluid channel has sides that are perpendicular to the inner floor of the first fluid reservoir.

36. A base for a housing as recited in claim 35, wherein said sides of said first fluid channel are parallel.

37. A base for a housing as recited in claim 30, wherein:

a. the cross section of said first fluid reservoir and taken in a plane parallel to the first inner floor is circular; and b. the cross section of said second fluid reservoir taken in a plane parallel to the second inner floor is circular.

38. A base for a housing as recited in claim 30, wherein said outlet stem comprises:

a. a first prong enclosing said first fluid passageway; and b. a second prong parallel to and separated from said first prong, said second prong enclosing said second fluid passageway.

39. A base for a housing as recited in claim 30, further comprising a cloison upstanding from the top of said interior wall interconnecting said pair of nonadjacent locations on the interior of said encircling sidewall.

40. A base for a housing as recited in claim 30, wherein the interior surface of the floor of said first fluid reservoir and the interior surface of the floor of said second fluid reservoir are coplanar.

41. A base for a housing as recited in claim 30, further comprising a continuous lip upstanding from the top of said encircling sidewall at the outer edge thereof.

42. In a vascular access port of the type having a needle-impenetrable housing that encloses a fluid reservoir with an inner floor, the fluid reservoir being accessible from the exterior of the housing through an access aperture sealed by a needle-penetrable septum, the vascular access port also having an outlet stem that projects from an outer wall of the housing and that encloses a fluid passageway extending longitudinally from the free distal end of the outlet stem to the housing, the improvement comprising an open-topped fluid channel communicating between the fluid reservoir of the housing and the fluid passageway of the outlet stem, the open top of said fluid channel being closed by a portion of the septum.

43. An access port as recited in claim 42, wherein the septum comprises:

a. a target dome positioned in the access aperture of the housing; and b. a septum web integrally formed with and encircling said target dome, said open top of said fluid channel being closed by a portion of said septum web.

44. An access port as recited in claim 43, wherein a side of said septum web opposite from said target dome defines a lower side of said septum web, and said open top of said fluid channel is closed by said lower side of said septum web.

45. An access port as recited in claim 43, wherein the thickness of said septum web is less than the thickness of said target dome.

46. An access port as recited in claim 43, wherein said septum web is substantially planar.

47. An access port as recited in claim 46, wherein the cross section of said target dome in a plane parallel to said septum web is substantially congruent to the cross section of the access aperture.

48. An access port as recited in claim 42, wherein said fluid channel is substantially linear, and the longitudinal axis of said fluid channel is disposed at an acute angle to the axis of the fluid passageway of the outlet stem proximal of the outlet stem.

49. An access port as recited in claim 42, wherein the sides of said fluid channel are perpendicular to the inner floor of the fluid reservoir.

50. An access port as recited in claim 49, wherein said sides of said fluid channel are parallel.

51. An access port as recited in claim 42, wherein said fluid channel communicates with the fluid passageway of the outlet stem at the end of the outlet stem remote from the free distal end thereof.

* * * * *